(12) United States Patent
David et al.

(10) Patent No.: US 11,717,581 B2
(45) Date of Patent: Aug. 8, 2023

(54) BACTERIAL LIGHT SOURCE WITH HIGH QUALITY OF LIGHT

(71) Applicant: Korrus, Inc., Los Angeles, CA (US)

(72) Inventors: Aurelien J. F. David, Los Angeles, CA (US); Philip Barton, Los Angeles, CA (US); Emil Radkov, Los Angeles, CA (US)

(73) Assignee: KORRUS, INC., Los Angeles, CA (US)

( * ) Notice: Subject to any disclaimer, the term of this patent is extended or adjusted under 35 U.S.C. 154(b) by 0 days.

(21) Appl. No.: 17/589,086

(22) Filed: Jan. 31, 2022

(65) Prior Publication Data

US 2022/0265872 A1 Aug. 25, 2022

Related U.S. Application Data

(60) Continuation of application No. 16/859,498, filed on Apr. 27, 2020, now Pat. No. 11,235,077, which is a division of application No. 15/633,425, filed on Jun. 26, 2017, now Pat. No. 10,632,214.

(60) Provisional application No. 62/354,464, filed on Jun. 24, 2016.

(51) Int. Cl.
| | |
|---|---|
| *A61L 2/00* | (2006.01) |
| *H05B 33/14* | (2006.01) |
| *A61L 2/08* | (2006.01) |
| *C09K 11/57* | (2006.01) |
| *C09K 11/77* | (2006.01) |
| *H01L 33/00* | (2010.01) |

(52) U.S. Cl.
CPC ............ *A61L 2/0052* (2013.01); *A61L 2/084* (2013.01); *C09K 11/57* (2013.01); *C09K 11/7715* (2013.01); *C09K 11/7728* (2013.01); *H01L 33/00* (2013.01); *H05B 33/14* (2013.01)

(58) Field of Classification Search
CPC ... A61L 2/0052; A61L 2/084; C09K 11/7715; C09K 11/7728; C09K 11/57; H01L 33/00; H05B 33/14
See application file for complete search history.

(56) References Cited

U.S. PATENT DOCUMENTS

| | | | |
|---|---|---|---|
| 8,398,264 | B2 | 3/2013 | Anderson |
| 8,740,413 | B1 | 6/2014 | Krames |
| 8,905,588 | B2 | 12/2014 | Krames |
| 8,933,644 | B2 | 1/2015 | David |
| 9,039,966 | B2 | 5/2015 | Anderson |
| 9,046,227 | B2 | 6/2015 | David |
| 9,289,622 | B2 | 3/2016 | Feng |
| 9,368,695 | B2 | 6/2016 | David |
| 9,410,664 | B2 | 8/2016 | Krames |

(Continued)

OTHER PUBLICATIONS

Stefani et al., Evaluation of Human Reactions on Displays with LED Backlight and a Technical Concept of a Circadian Effective Display, SID 10 Digest, ISSN 0097-966X/10/4102-1120, 2010, 4 pgs.

*Primary Examiner* — Sean E Conley
(74) *Attorney, Agent, or Firm* — FisherBroyles LLP

(57) ABSTRACT

A light source for emitting emitted light having an SPD comprising: (a) a plurality of light emitters including at least one violet solid-state emitter; (b) at least one phosphor; wherein said light emitters and said at least one phosphor being configured such that: at least 25% of the power within the SPD is in the range 390-420 nm, and the emitted light has a chromaticity which is within a Duv distance of less than 5 points from the Planckian locus.

5 Claims, 20 Drawing Sheets

(56) References Cited

U.S. PATENT DOCUMENTS

| | | |
|---|---|---|
| 9,677,723 B2 | 6/2017 | David |
| 9,839,706 B2 | 12/2017 | Anderson |
| 10,076,633 B2 | 9/2018 | Krames |
| 10,137,277 B2 | 11/2018 | Krames |
| 10,147,850 B1 | 12/2018 | Krames |
| 2013/0313516 A1 | 11/2013 | David |

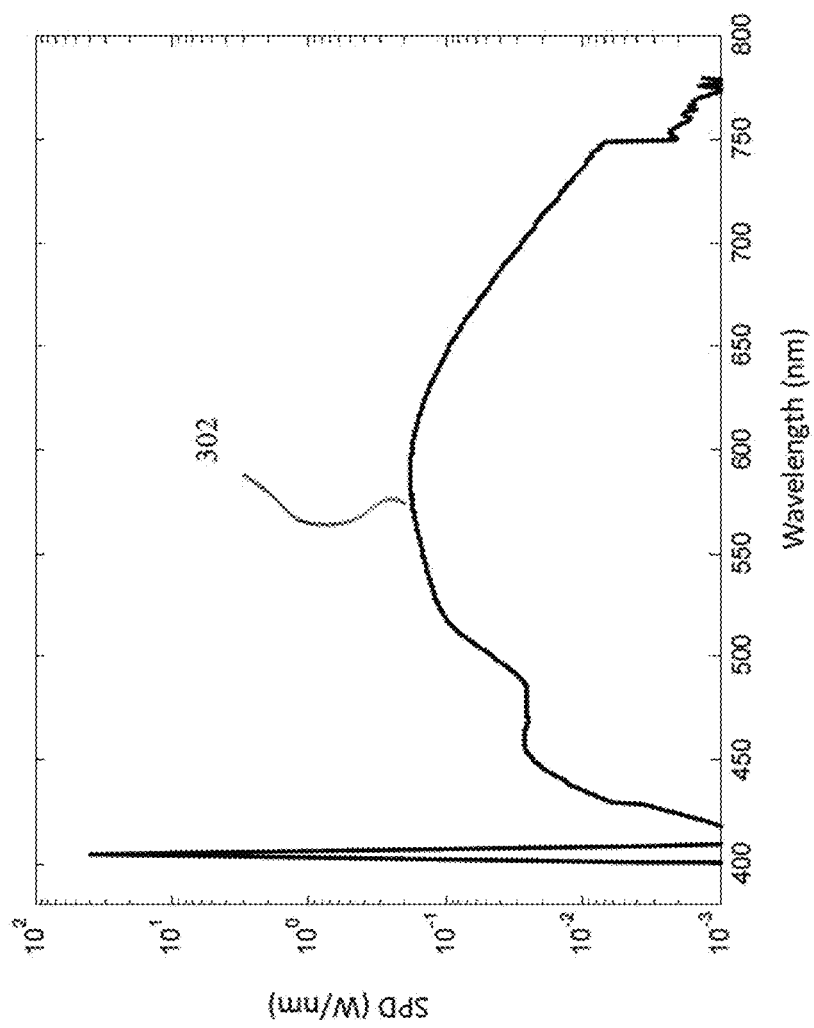

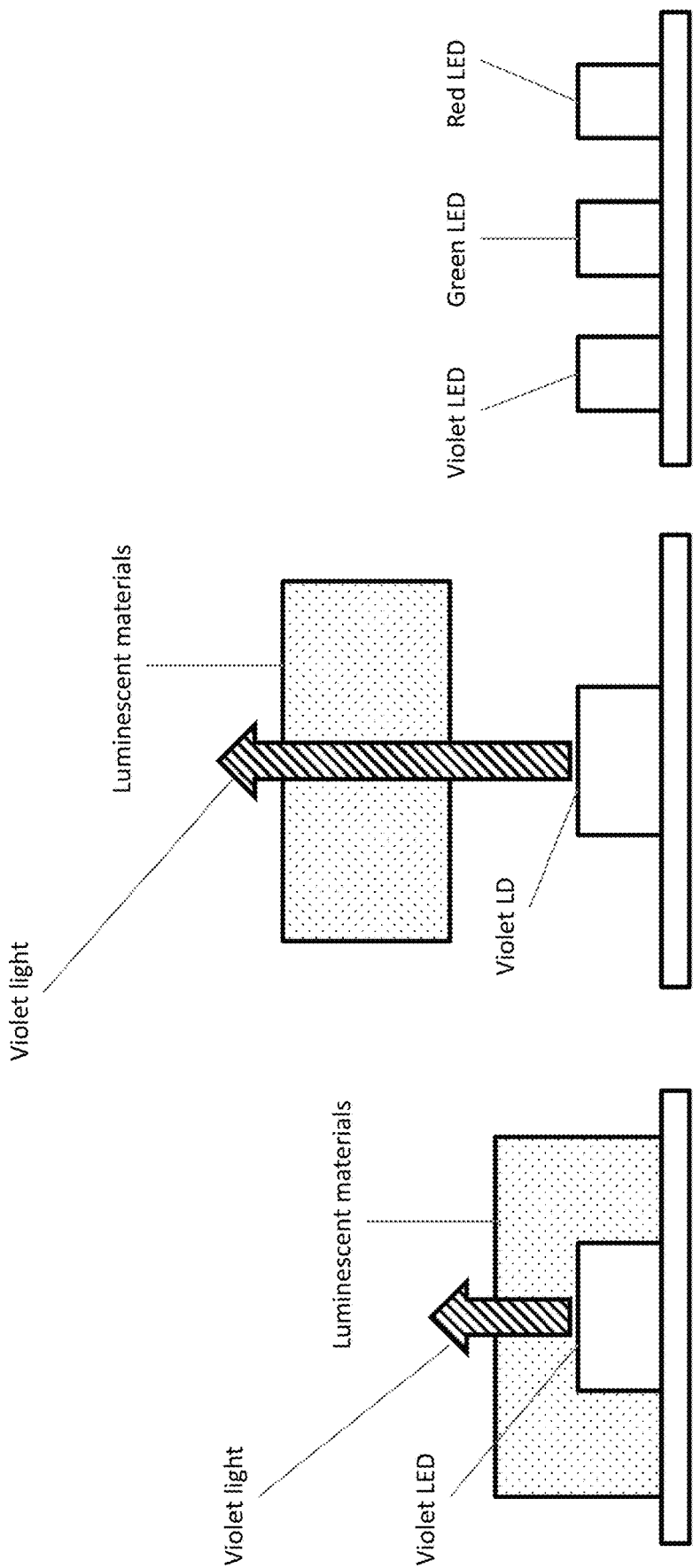

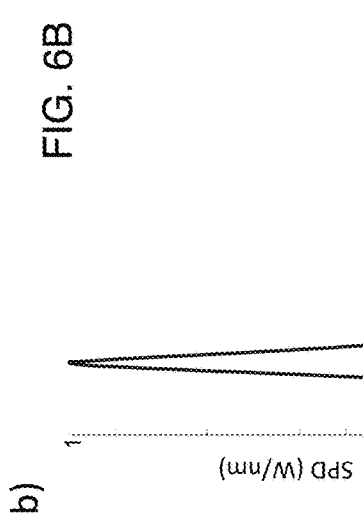
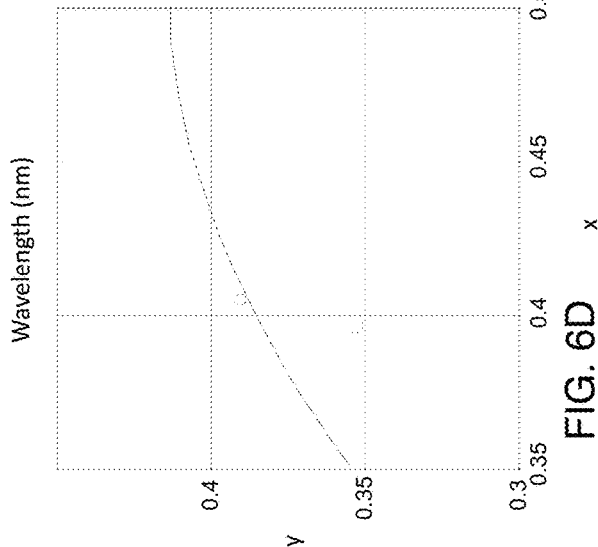
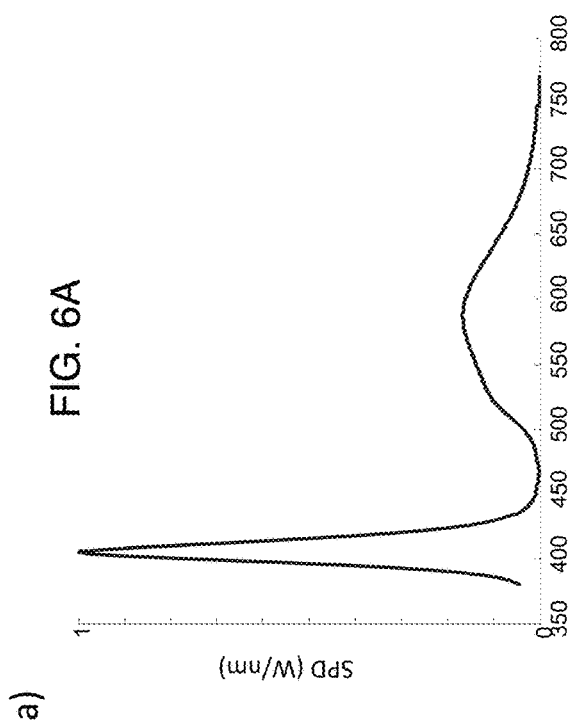
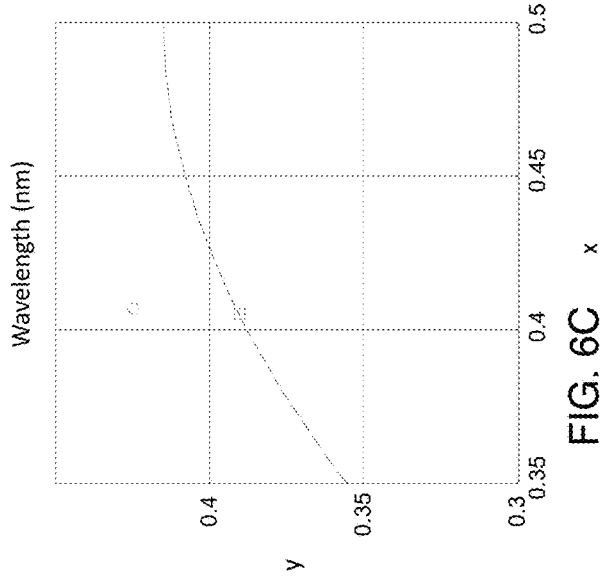
FIG. 6A
FIG. 6B
FIG. 6C
FIG. 6D (a) -Dxy in 10° for SPD targeted in 2°

(b) Dxy in 2° for SPD targeted in 10°

BACTERIAL LIGHT SOURCE WITH HIGH QUALITY OF LIGHT

REFERENCE TO RELATED APPLICATION

This application is a divisional of U.S. application Ser. No. 15/633,425, filed Jun. 26, 2017, which is based on U.S. Provisional Application No. 62/354,464, filed Jun. 24, 2016, hereby incorporated by reference in its entirety.

FIELD OF INVENTION

The present invention relates, generally, to a light source, and, more specifically, to a bactericidal light source with a high quality of light.

BACKGROUND

It has recently been discovered that a high flux of illumination by 405 nm radiation could have a significant desirable bactericidal effect. Following this, some companies have proposed creating a white light emitter having a large violet peak, which could provide general-illumination light at the same time as a bactericidal effect. The conventional approach is to combine standard white light emitting diodes (LED)s with violet LEDs emitting at 405 nm.

Applicants recognize, however, that this approach leads to light having poor chromaticity. Chromaticity may be quantified through use the Cartesian distance in (u v) space, known as Duv, or in (x y) space, known as Dxy. For a target chromaticity (for instance, that of a Blackbody radiator at 3000 K), Duv is calculated as the Cartesian distance between that target chromaticity and the light source's actual chromaticity in (u, v) space. In some cases, the distance is computed between a point and a curve—for instance, between the chromaticity of a spectrum (a point) and the Planckian locus (a curve). The distance is the closest distance from the point to the curve (i.e. the distance from the point to its orthogonal projection on the curve, in the space of interest). This concept is commonly used in color science to express how closely an SPD replicates the chromaticity of a blackbody radiator. Color distances may be expressed in values of Duv or Dxy. As known, Duv and Dxy are related. Typically, a Duv value is about half of the corresponding Dxy value (with some variation depending on the specific direction of the color shift). In particular, for shifts substantially along the +/−y direction (as is the case in some embodiments shown herein), this ratio is 0.5. This conversion factor may be used to translate from one distance metric to the other.

FIGS. 1a and 1b illustrate the poor chromaticity of the conventional approach of combining standard white light emitting diodes (LED)s with violet LEDs emitting at 405 nm. In FIG. 1a, light emitted from a standard white LED (white spectrum 102, on-Planckian with correlated color temperature (CCT)=3000 K, Ra=80, R9~0) is combined with a large violet peak from a violet LED (violet spectrum 104, having a peak at 405 nm). The resulting spectrum 106 (has a high violet content, and may be suitable for bactericidal purposes. However, the addition of the violet peak pulls the chromaticity to a higher CCT (3200K) and far below-Planckian (Duv=−0.0177), resulting in an uncontrolled very pronounced pink tint.

Furthermore, depending on the amount of violet light, the resulting chromaticity may occur at any uncontrolled color point, which can be undesirable in applications where a controlled chromaticity (often, substantially on-Planckian) is wanted. This is further illustrated in FIG. 1b. FIG. 1b shows the chromaticity (in x-y diagram) of the same standard white LED, when combined with various amounts of violet light. Curve 108 is the Planckian locus. The percent values shown on FIG. 1b correspond to the violet fraction, i.e. the fraction of the spectral power distribution (SPD) in the range 390-420 nm. At 0% violet, the source is on-Planckian. In other words, a standard white LED comprising 0% violet is on-Planckian. As the violet fraction increases to 10%, 20%, and 30%, however, the chromaticity is pulled below-Planckian, and the emitted light is no longer white. This is characterized by the Duv distance from the Planckian locus—i.e., −0.0044, −0.0102 and −0.0177, respectively.

The large values of Duv distance from Planckian demonstrate that it is not possible to add much violet light and remain near the Planckian locus with this approach, while emitting white light. The last point of FIG. 1b has 30% violet, and corresponds to the SPD of composite spectrum 106 of FIG. 1a. Therefore, there is a need for a light source with a spectrum having a large fraction of violet light but retaining desirable quality of white light. The present invention fulfills this need among others.

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Applicants have found that it is possible to design particular spectra, through a careful configuration of LEDs and phosphor formulations, which can provide a large fraction of violet light together with high quality of light. For example, it is known that in some cases, an SPD having a controlled amount of violet light can yield desirable properties for quality of light. For instance, a violet amount of 3-10% for a spectrum at 3000K can increase the color rendering index (CRI) and can improve the rendition of whiteness for objects having fluorescing agents.

Although Applicants have determined the need for a light source, which has a spectrum having a large fraction of violet light, but which retains desirable quality of light, the desirability of this is type of light source is generally contrary to conventional thinking. Specifically, one skilled in the art of LED lighting would typically not design an LED whose spectrum has such a large amount of violet light. Indeed, the human eye is much less sensitive to violet light than it is to blue light. As a result, when the amount of violet light in a spectrum is increased, the luminous efficacy of radiation (LER) of the resulting spectrum decreases. LER quantifies the lumens per optical watts in the SPD, and describes how brightly an SPD is perceived by our vision system. A common goal of LED lighting is to increase LER.

To achieve a white spectrum having a high LER, the natural choice is to include blue light in the spectrum, and to either have no violet light whatsoever (conventional approach of blue-pumped LED with phosphor conversion) or to retain a small fraction of violet light (typically 3-10% for warm-white light sources) to improve color rendition without exceedingly decreasing LER. Therefore, increasing the violet fraction to a very high value is contrary to common practice in efficient LED lighting. A slightly higher fraction of violet light may be suitable for a higher-CCT light source, however, for common CCTs (in the range 2700K-6000K) the violet fraction remains moderate in general lighting applications.

Accordingly, one aspect of the invention is a spectrum having a relatively high component of violet light (around 405 nm) in the final spectrum. By varying the amount of violet and blue radiation a desired chromaticity and violet fraction can be achieved. The violet component can be calculated by computing the fraction of the SPD which falls in the violet range. This can be expressed in different ways, including a percent of the total power in the SPD. In one embodiment, the violet range is 390 nm-420 nm. Therefore, the "violet fraction" in the following will be computed as the ratio of the power of the SPD in the range 390-420 nm, to the total power of the SPD (in practice, for LED sources, the total power can often be computed by considering the range 380-780 nm since very little radiation lies outside this range). Another way to quantify bactericidal effects is in terms of watts per lumens: this quantifies how many watts fall in the violet range of interest (for instance, 390-420 nm) for a spectrum emitting one lumen of light.

Furthermore, Applicants recognize that traditional color matching functions (CMFs) used to calculate chromaticity, and thus to target a spectrum's proximity to the Planckian locus, are inaccurate for spectrums having a large component of violet. Specifically, Applicants conducted experiments which demonstrate that the original CIE 1931 2° CMFs are not as accurate as 10° CMFs, especially at short wavelengths. For example, using the 1964 10° CMFs yielded a much better perceptual match of chromaticity. In other words, if a source having a large violet fraction is designed to be on-Planckian (at a given CCT) according to the 10° CMFs, this source has a perceived chromaticity which is close to a blackbody radiator (i.e. a filament lamp) at the same CCT. In contrast, if color targeting is performed with 2° CMFs, the perceived chromaticity may have a pronounced pinkish tint. Therefore, unless otherwise specified, chromaticity is calculated using CIE 1964 10° CMFs because of its accuracy at shorter wavelengths.

In one embodiment, the invention relates to a light source for emitting emitted light having an SPD comprising: (a) a plurality of light emitters including at least one violet solid-state emitter; (b) at least one phosphor; wherein said light emitters and said at least one phosphor being configured such that: at least 25% of the power within the SPD is in the range 390-420 nm, and the emitted light has a chromaticity which is within a Duv distance of less than 5 points from the Planckian locus calculated using 1964 10° CMFs.

In another embodiment, the invention relates to a light source for emitting emitted light having an SPD comprising: a plurality of light emitters including at least one violet solid-state emitter; and at least one phosphor; wherein the light emitters and said phosphor are configured such that: the SPD is characterized by a ratio of power in the range 390-420 nm to lumens which is above 0.5 mW/lm, and the emitted light has a chromaticity which is within a Duv distance of less than 5 points from the Planckian locus calculated using 1964 10° CMFs.

In yet another embodiment, the invention relates to a method of reducing bactericidal counts, the method comprising: (a) powering a light source to emit emitted light having a chromaticity, said light source comprising a plurality of light emitters including at least one violet solid-state emitter and at least one phosphor, herein said chromaticity is within a Duv distance of less than 5E-3 from the Planckian locus calculated using 1964 10° CMFs; and (b) configuring said light source to illuminate a surface with said emitted light to reduce a bacterial count by at least a factor of ten in twelve hours.

BRIEF DESCRIPTION OF FIGURES

FIG. 3 illustrates spectrum generated by a laser LED and at least one other LEDs according to one or more embodiments of the invention.

FIGS. 4a-4C illustrate various light source configurations according to one or more embodiments of the invention.

FIG. 6a-6d illustrate the spectral power distributions according to one or more embodiments of the invention.

DETAILED DESCRIPTION

Figure 19:
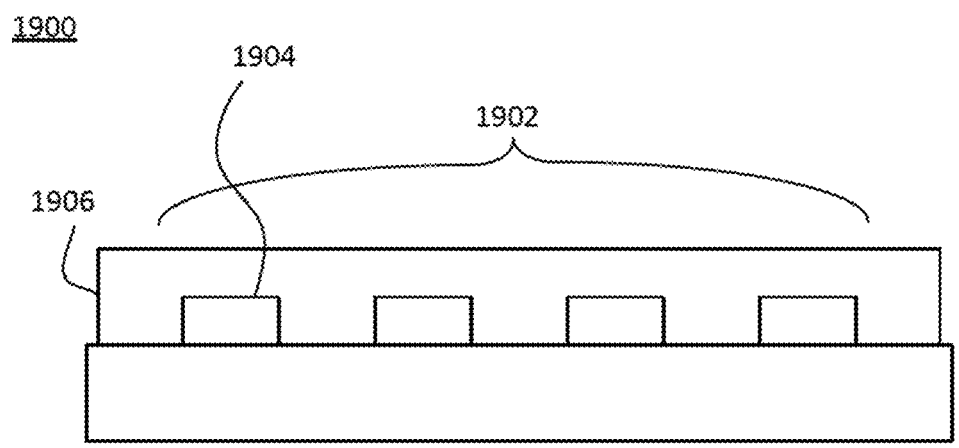
FIG. 19 illustrates a light source according to one or more embodiments of the invention.

FIG. 19 illustrates an embodiment of light source 1900 for emitting emitted light having a spectral power distribution. In the illustrated embodiment, the light source 1900 includes a plurality of light emitters 1902 and at least one phosphor 1906. The plurality of light emitters 1902 has at least one violet solid-state emitter 1904. In one embodiment, the plurality of light emitters 1902 and the at least phosphor 1906 are configured such that at least 25% of the power within the SPD is in the rage of 390-420 nm, and the emitted light has a chromaticity which is within a Duv distance of less than 5E-3 from the Planckian locus, as calculated with 1964 10° CMFs. In another embodiment, the plurality of light emitters 1902 and the at least phosphor 1906 are configured such that the SPD is characterized by a ratio of power in the range of 390-420 nm to lumens which is above 0.5 W/lm, and the emitted light has a chromaticity which is within a Duv distance of less than 5 points from the Planckian locus. In yet another embodiment, the plurality of light emitters 1902 and the at least phosphor 1906 are configured such that at least 15% of the power within the SPD is in the range of 390-420 nm, and a first distance of the SPD's chromaticity to the Planckian locus computed with 1931 2° CMFs is greater than a second distance of the SPD's chromaticity to the Planckian locus calculated using CIE 1964 10° CMFs.

While the embodiment of FIG. 19 illustrates that the at least phosphor 1906 is disposed over each of the plurality of lights emitters 1902, in one more embodiments, at least one of the plurality of emitters 1902 may be disposed outside that at least one phosphor 1906 such that light emitted by the light source is not converted by the phosphor. Further, in other embodiments, each of the plurality of light emitters 1902 may be coupled to discrete a phosphor or phosphors. In such embodiment, one or more of the plurality of light emitters 1902 may not be coupled to a phosphor.

In one embodiment, the plurality of light emitters 1902 may be any suitable light emitters able to obtain a desired SPD. For example, the plurality of light emitters 1902 may be solid state emitters (LEDs or Lasers). Different light emitters at different wavelengths may be used. At least one emitter may have a peak wavelength around 405 nm or in a range 400-410 nm or 395-415 nm, to provide bactericidal effect. At least one emitter may have a peak wavelength in a blue range (or in a range 430-490 nm or 440-460 nm). Further, the at least one phosphor 1906 may include any number and type of phosphors (luminescent materials) able to obtain a desired SPD, including blue, green, yellow and red phosphors. The phosphors may be configured to convert light from some of all light emitters, for instance they absorb violet light but no blue light or vice-versa.

Various aspects of quality of light are addressed below, including: correlated color temperature (CCT); distance from the Planckian locus (Duv); chromaticity of the light (including perceptual chromaticity); color rendering index (CRI) (general index Ra and special red index R9); IES TM-30-15 color metrics (including Rf, Rg, and special indices such as the red rendering index Rfh1); Cyanosis Observation Index (COI) (as described in document AS/NZS 1680.2.5:1997).

Although the range 390-420 nm is illustrated herein, it should be understood that, in various embodiments, other ranges centered at or near 405 nm are also suitable. In other embodiments, the violet range is 400-410 nm, 400-420 nm, 400-430 nm, 380-430 nm. In some embodiments, a preferred peak wavelength is selected (such as 400 nm, 405 nm, 410 nm, 415 nm, 420 nm, 425 nm) and the violet range is a window of +/−1 nm or 2 nm or 5 nm or 10 nm or 15 nm or 20 nm around this peak. Further, the violet content may be quantified various different ways. (e.g., by integrating the violet light with a bactericidal action spectrum, which may peak around 405 nm). One skilled in the art will know to translate the following teachings to a different quantification of violet content, in order to design new spectra having a large violet content and a high quality of light. Accordingly, as the science of bactericidal effects of violet light is refined, improvements to the spectrum's detailed violet content are envisioned, and can benefit from the present teachings.

On-Planckian Sources with a Large Violet Fraction

The term white chromaticity qualitatively describes light having a white appearance. This can be quantified in several ways. In various embodiments, white light is light along the Planckian (Blackbody) locus or along the locus of CIE daylight. In some embodiments, white light is light having chromaticity coordinates within an ANSI quadrangle or MacAdam ellipse defining white light [as described in ANSI C78.277 2015]. In other embodiments, white light is light slightly below the Blackbody locus, along the "white locus" studied by researchers at RPI. The RPI white locus is a curve in the x-y coordinate space which is distinct from the Blackbody locus. It may be used for color targeting or to define a desired chromaticity. In some embodiments, the light source's chromaticity is within a distance less than 5e-3 from the white locus, when computed with the 1964 10° CMFs.

Alternatively, in a specific application, the target chromaticity is intentionally offset below the Planckian. For instance, the target chromaticity may be defined by a specific CCT and a specific distance below-Planckian (such as Duv=1e-3, 2e-3, 3e-3, 5e-3, 1e-2). In some embodiments, the light source's chromaticity is within a distance less than 5e-3 from this target chromaticity, when computed with the 1964 10° CMFs. Some embodiments are methods to target a light source chromaticity according to these principles.

In various embodiments, emitted light has a "normal" CCT (depending on the application, the CCT could be in the range 2000K-7000K, 2700K-6500K, in the range 2700K-5000K, in the range 3000K-5000K, in the range 2700K-3000K, or substantially at 2700K or 3000K or 3500K or 4000K or 5000K or 6500K) and having a large amount of violet light (in the range 20%-70%, 25%-50%, 30-40%, or substantially 10%, 15%, 20%, 25%, 30%, 35%, 40%, 45%, 50%, 60%, 65%, 70%), while retaining a white light chromaticity. In a variety of embodiments, the violet light has a spectral peak around 405 nm (i.e. substantially at peaking in the range 400-410 nm, or at 400 nm, 401 nm, 403 nm, 404 nm, 405 nm, 406 nm, 407 nm, 408 nm, 409 nm, 410 nm).

In various embodiments, the emitted light is characterized by a distance Duv from a desired chromaticity which is less than a predetermined value. In some embodiments, the desired chromaticity may lie on the Blackbody locus or on the CIE daylight locus. In some embodiments, the predetermined value may be less than 15E-3, less than 10E-3, less than 6E-3, less than 4E-3, less than 2E-3, less than 1E-3, less than 0.5e-3. In terms of the well-known MacAdam ellipses, a Duv distance of ±0.006 is approximately equivalent to a 7-step MacAdam ellipse. Therefore, the predetermined value may for instance correspond to a MacAdam ellipse which is less than 7 steps, 5 steps, 3 steps, 1 step.

In many embodiments, retaining a white chromaticity within the emitted light is not trivial because, as the amount of violet light is raised (for instance to a violet fraction of 20-40%), the chromaticity tends to drift below the Planckian locus in the violet direction. To compensate for this, in various embodiments, the amount of blue light in the spectrum of the emitted light is reduced. Further, as the human eye is much less sensitive to violet (e.g. 405 nm) than to blue (e.g. 450 nm), it takes a lot of violet light to achieve the same chromaticity balance as would be obtained with relatively little blue light in a spectrum. Therefore, embodiments achieve a white chromaticity on the Planckian locus with very little blue light and a large amount of violet light. This may be useful for applications such as bactericidal lighting, or circadian-friendly lighting (for instance, SPDs having little blue radiation in the range 440-490 nm). In other cases, the present teachings may however also be relevant to sources having little or no violet light. For instance, some sources having very narrow bandwidths (such as sources having laser peaks) or an absence of radiation in a wide wavelength range may likewise suffer from inaccurate predictions with standard 2° CMF targeting regardless of their violet content—this may happen because the SPD samples the CMFs in a region where they are inaccurate (which may be in the short-wavelength range or in anther range, including crossover regions where two cone fundamentals cross over, such as around 460-470 nm or 540-560 nm). Therefore, the present teachings regarding use of suitable CMFs and other chromaticity-matching methods may apply to general lighting and to display. In some cases, they apply to embodiments emitting an SPD having at least a spectral peak with a FWHM less than 20 nm (or 10 nm or 5 nm) which carries at least 5% of the SPD's power. In some cases they apply to embodiments emitting an SPD having a low-radiation region, where low-radiation region may be a wavelength region of at least 50 nm (or 30 nm or 80 nm) located in the visible range 400 nm-700 nm (or 450 nm-650 nm) such that less than 5% (or 2% or 1% or 0.5%) of the SPD is present in this wavelength range. Embodiments may include sources having a large discrepancy (such as Duv>0.001, 0.003, 0.005, 0.01, or Dxy>0.001, 0.003, 0.005, 0.01, 0.02) between chromaticities according to two distinct CMFs, for instance between 1931 2° CMFs and 1964 10° CMFs. Embodiments may include a method of color-targeting such SPDs.

Figure 1B:
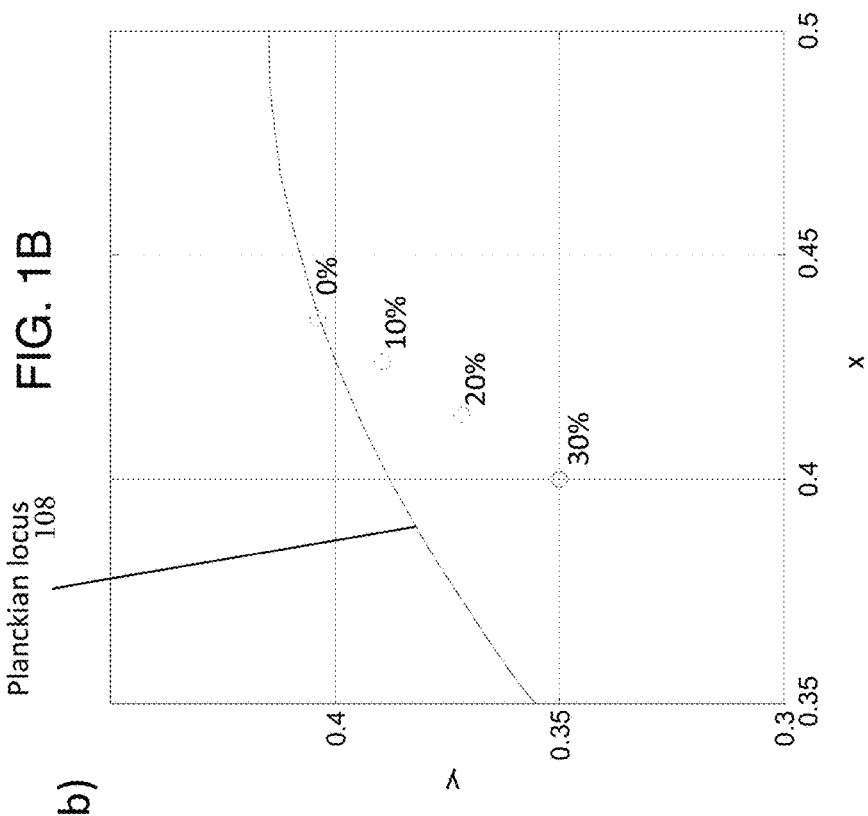
FIGS. 1a and 1b illustrate a spectrum and corresponding chromaticity generated by the combination of different types of LEDs according to one or more embodiments of the invention.
Figure 1A:
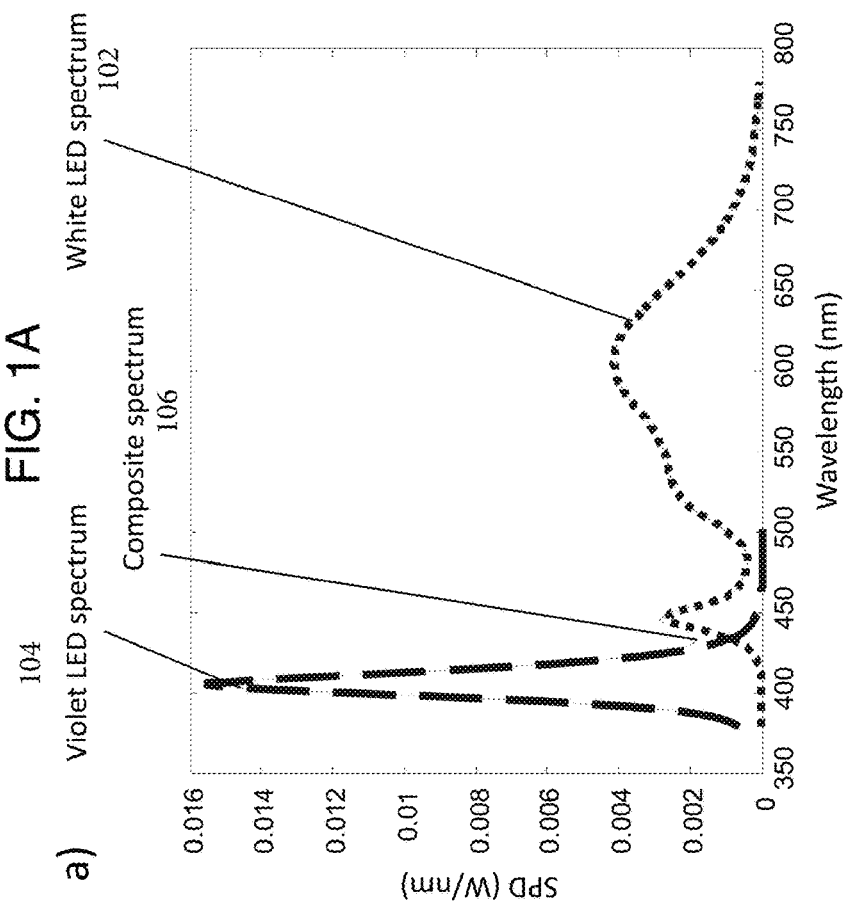
Figure 2B:
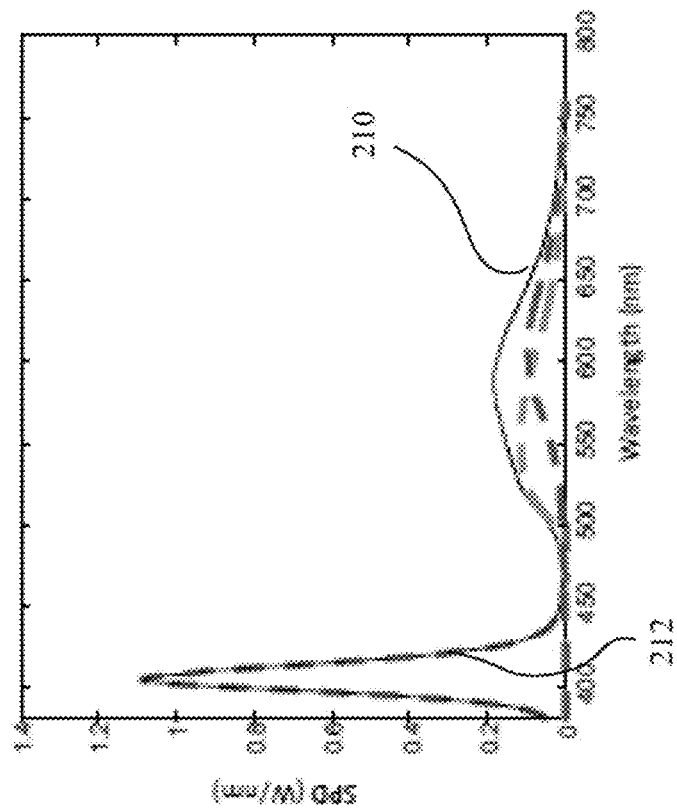
FIGS. 2a, and 2B illustrate spectra generated by various combinations of LEDs according to one or more embodiments of the invention.
Figure 2A:
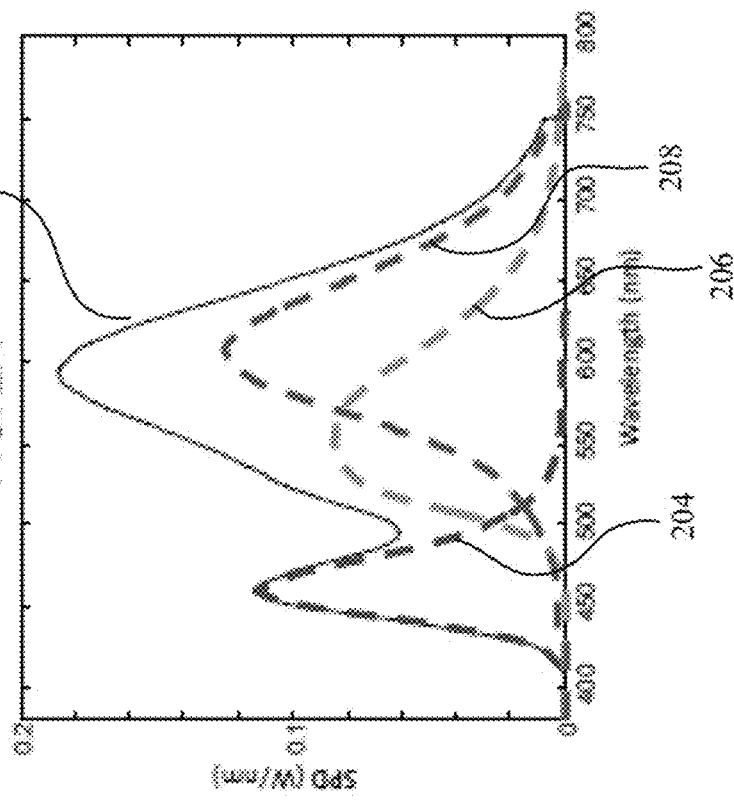

FIG. 2a is prior art and shows a spectrum 202 having standard SPD with a CCT of 3000K formed of blue light spectrum 204, green light spectrum 206 and red light spectrum 208. FIG. 2b illustrates a spectrum 210 having the same chromaticity, the same number of lumens as spectrum 202, but having a violet LED peak (violet light spectrum 212) instead of a blue LED peak (blue light spectrum 204). This SPD of spectrum 210 has a violet fraction of 42% and, in one embodiment, is obtained by combining spectra representative of a green silicate phosphor, a red nitride phosphor and a violet LED. In other embodiments, other phosphors having similar spectra may be alternatively used. For example, in one or more embodiments, the use of a green beta-sialon phosphor may be suitable.

Figure 17:
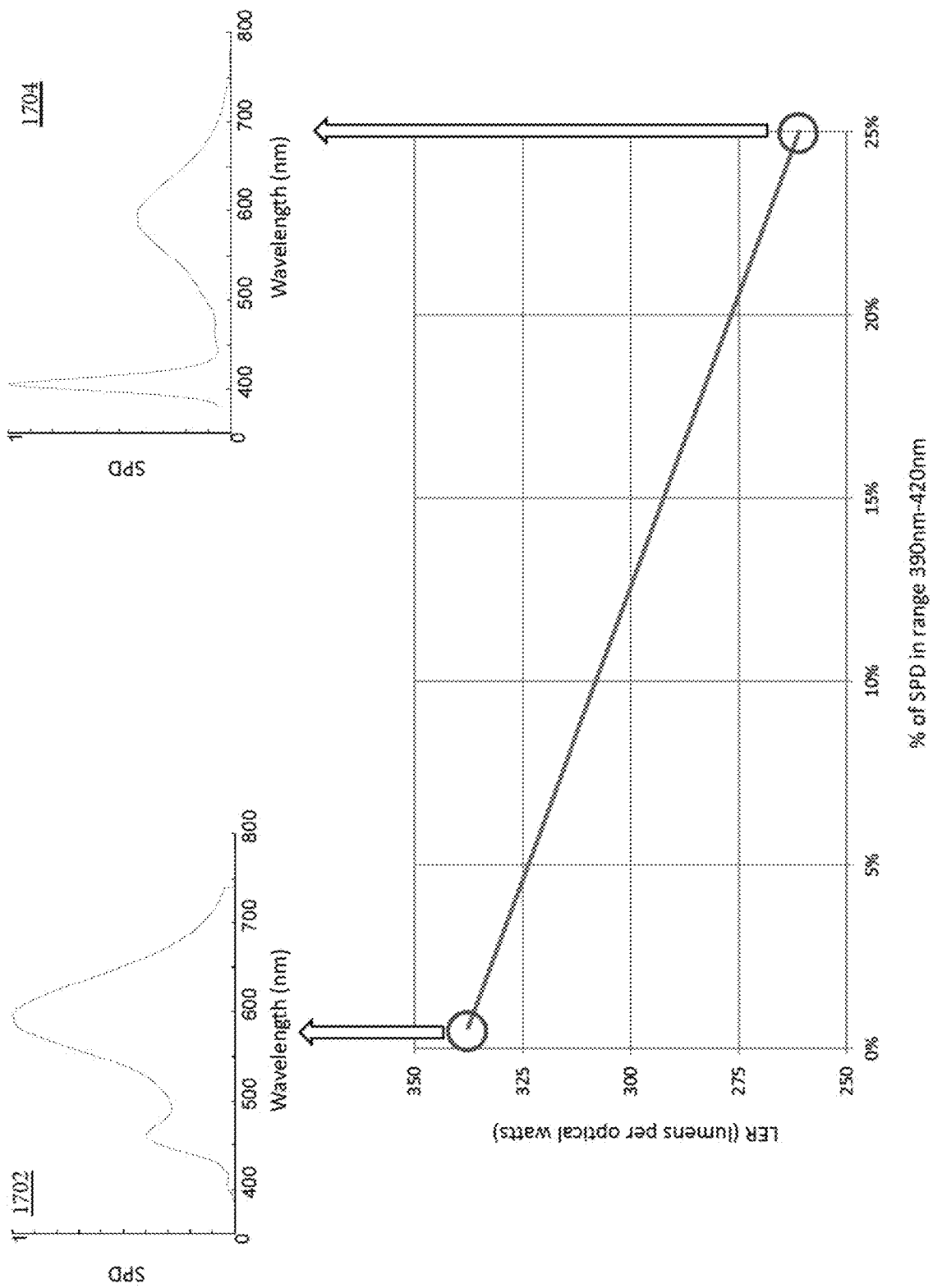
FIG. 17 illustrates the tradeoffs in spectral power distribution based on the amount of violet and blue radiation according to one or more embodiments of the invention.

In one embodiment, the reduction of blue light in the spectrum of emitted light may be achieved in several ways. In one embodiment, the spectrum may be created with a violet pump die, a green phosphor and a red phosphor, but no blue phosphor. Alternatively, a notch optical filter which cuts off light in the blue range may be used. Such filters can be absorbing filters or dichroic filters, or similar filters. In some cases, a violet-green-red spectrum is combined with a filter to further cut off blue content. In some embodiments, the amount of blue radiation is not completely eliminated but merely reduced. For instance, blue radiation may originate from a phosphor or an LED or other solid-state-lighting emitter, whose intensity is selected to achieve a desired violet fraction. This is shown on FIG. 17, where the amount of violet and blue radiation is traded off to achieve a constant chromaticity with a varying violet fraction. As shown in FIG. 17, the respective amount of blue and violet radiation can be traded off to achieve a desired chromaticity and a desired violet content. SPDs 1702 and 1704 show the end points of this process, with near-maximal blue emission (1702) or violet emission (1704). Other embodiments along the curve of FIG. 17 combine a violet emission and a blue emission.

In particular, some embodiments may include the use of very high efficiency GaN-based violet emitters on bulk GaN, as demonstrated by assignee in U.S. patent application Ser. No. 12/884,848, filed Sep. 17, 2010, and Hurni15.

In one or more embodiment, the light source or sources are solid-state light emitters. In some embodiments, a violet laser diode is used instead of a violet LED. In one or more embodiments, laser diodes provide a narrow spectrum (which may be narrower than 0.1 nm or 0.5 nm or 1 nm or 2 nm, quantified as a full-width at half maximum or a full width at 90% of maximum). In various embodiments, a narrow spectrum with a peak near 405 nm provides violet radiation at the peak efficiency for bactericidal effect, in contrast to an LED which may have emission tails at shorter and longer wavelengths.

FIG. 3 shows a spectrum 302 having a laser line at 405 nm and a green and a red phosphor. It is shown on log vertical scale as the very sharp violet line would hide the rest of the spectrum in linear scale. The spectrum 302 is on-Planckian with CCT=3000K, and has a very high violet fraction of 65%. The spectrum 302 is obtained by combining spectra representative of a green silicate phosphor, a red nitride phosphor and a violet LED—although other phosphors having similar spectra would also be suitable. For instance, use of a green beta-sialon phosphor or a yellow or green garnet phosphor may be suitable.

Similarly, violet LEDs with improved properties having a narrower emission—typically peaking near 405 nm—can be used. Narrow emission can be obtained by optimizing the epitaxial properties of the LED emitter. Although the spectra shown in this application are representative of inorganic III-Nitride LEDs with InGaN quantum wells, other light emitters (LEDs and lasers, inorganic and organic, various materials systems) can be envisioned to emit violet light.

In the case of InGaN emitters, for instance, the active region of the LED comprises InGaN layers. By selecting the composition of these layers (amount of In and Ga), as well as their thickness, one can tune the emitter's emission wavelength to a desired value such as 405 nm, as is known in the art.

In some embodiments, direct emission of green and/or red light may be used instead of a phosphor. For instance the light source may consist of a violet emitter (LED or laser) combined with a green LED and a red LED; or a green phosphor and a red LED, or a green LED and a red phosphor.

In some embodiments comprising phosphors, the phosphors are directly excitable by the violet emitter.

FIG. 4a shows a violet LED optically coupled to a matrix of luminescent materials (such as phosphors). The light from the LED pumps the phosphors, to generate a spectrum such as those taught in this disclosure. FIG. 4b shows an alternate configuration with a laser optically coupled to a luminescent material. FIG. 4c shows a violet-green-blue system of direct emitters.

Figure 5:
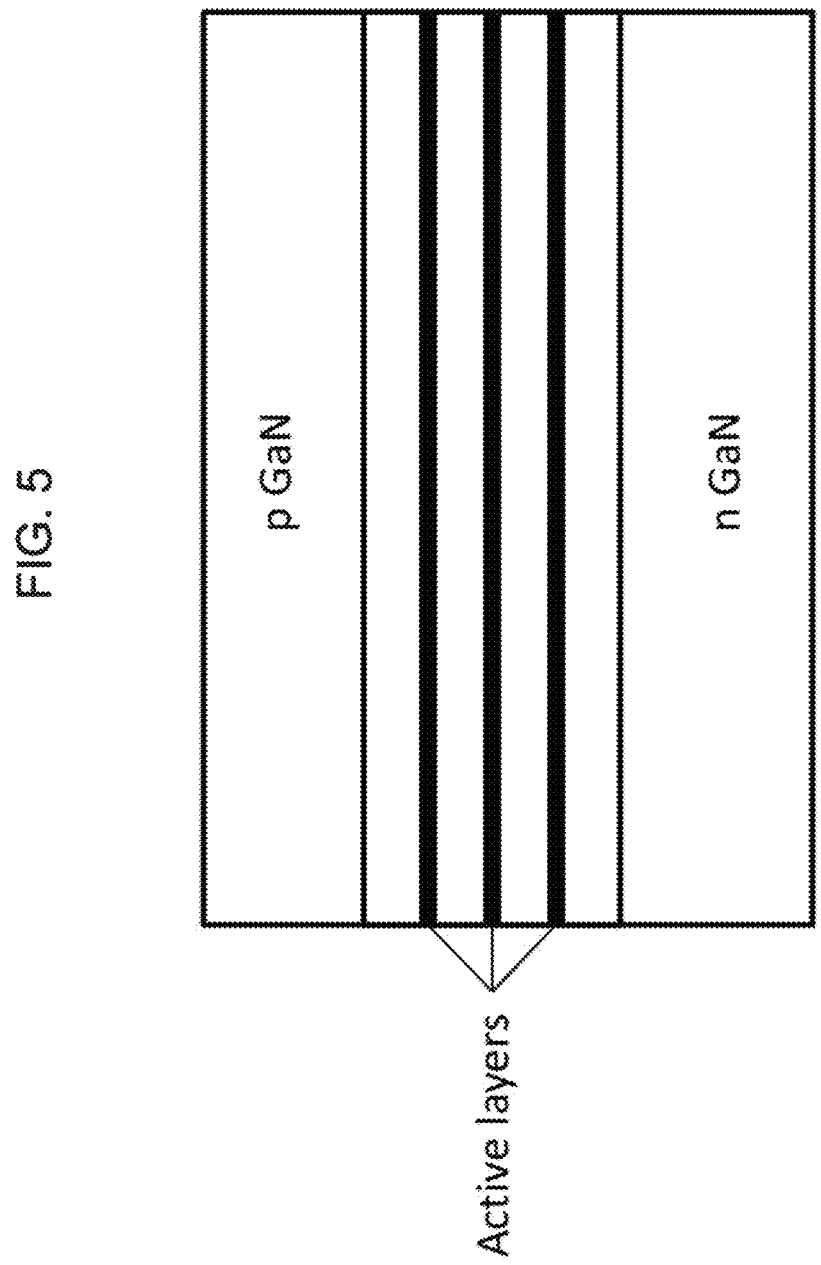
FIG. 5 illustrates a cross-section of the epitaxial layers of an LED according to one or more embodiments of the invention.

FIG. 5 shows a schematic cross-section of the epitaxial layers of an LED, including the n-doped GaN layers, the p-doped GaN layers and the active layers. The active layers may contain InGaN and be configured to emit near 405 nm.

In some embodiments, the spectrum is on-Planckian when calculated with other color matching functions (CMFs) than the original CIE 1931 2° CMFs. Applicants have discovered that this may be desirable because the 2° CMFs are inaccurate, especially at short wavelength. Experiments in our laboratories have demonstrated that using the 1964 10°

CMFs yielded a much better perceptual match of chromaticity; in other words, if we design a source having a large violet fraction to be on-Planckian (at a given CCT) according to the 10° CMFs, this source has a perceived chromaticity which is close to a blackbody radiator (i.e. a filament lamp) at the same CCT. In contrast, if color targeting is performed with 2° CMFs, the perceived chromaticity may have a pronounced pinkish tint. Besides the CIE 1964 10° CMFs, one skilled in the art will know to use other modern CMFs such as those developed by CIE TC 1-36 (which can be derived at any relevant viewing angle, including 2°, 10° and others, as well as for specific age groups by taking into account the reduced short-wavelength sensitivity caused by aging).

Resources on modern CMFs, and related data, can for instance be found at http://www.cvrl.org/cmfs.htm. CMFs of interest for this invention include the 1964 10° CMFs, and the 2005 2° and 10° CMFs (developed by TC 1-36, and also called physiologically-relevant XYZ functions).

Given a set of CMFs (x, y z) and an SPD S, chromaticity is calculated as follows: X=int(S·x), Y=int(S·y), Z=int(S·z), x=X/(X+Y+Z), y=Y/(X+Y+Z), z=Z/(Z+Y+Z). Here int( ) denotes the integral over wavelength.

Figure 20:
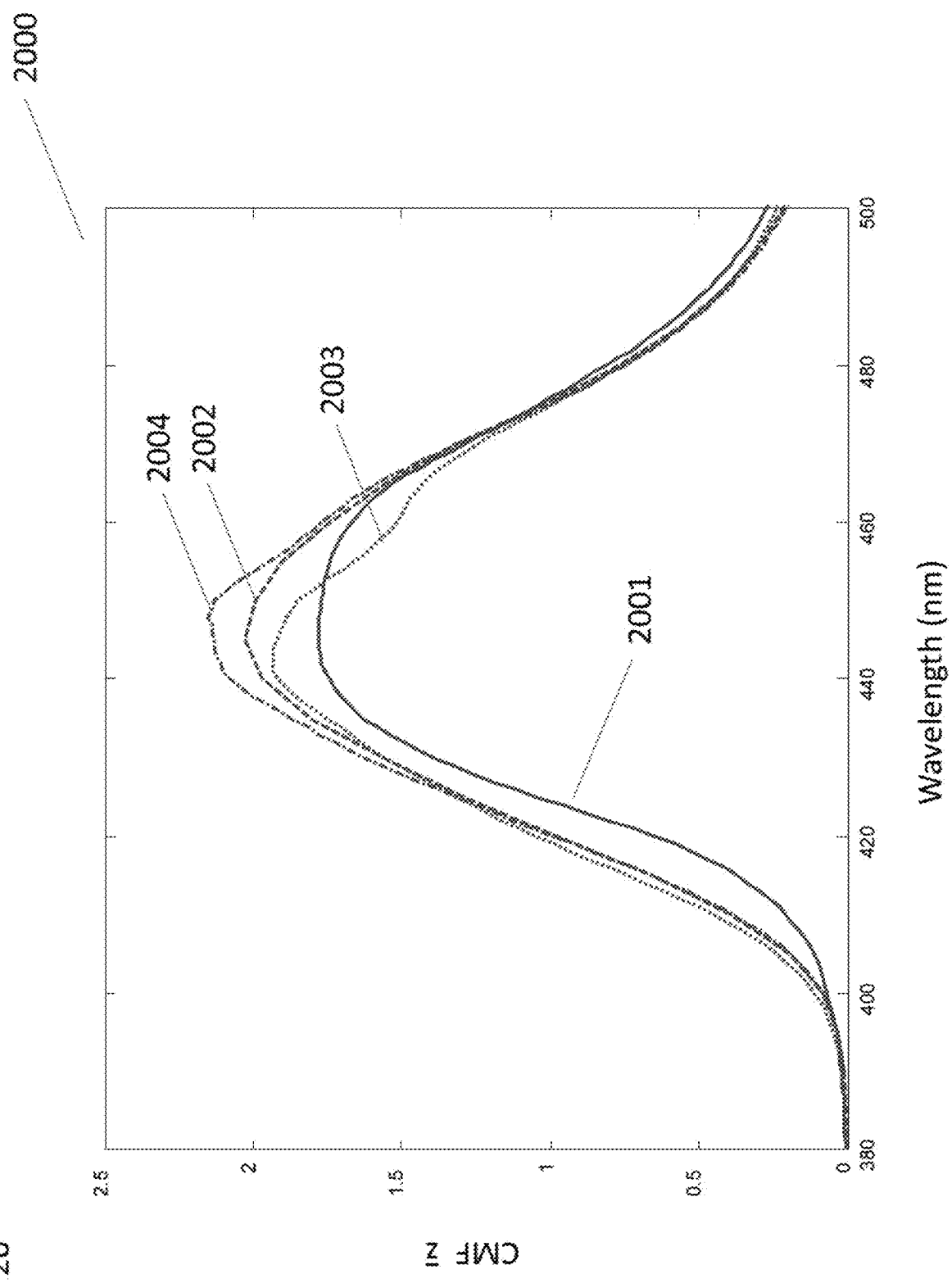
FIG. 20 is a graph illustrating the difference between various CMFs according to one or more embodiments of the invention.

FIG. 20 illustrates the difference between various CMFs. Plot 2000 shows the third CMF z in four cases: 1931 2° (2001), 1964 10° (2002), 2005 2° (2003), 2005 10° (2004). The discrepancy in z has been found to largely drive the discrepancy in some chromaticity predictions discussed in this Application, because z is the CMF which is most sensitive to short-wavelength. FIG. 20 shows that, while all four z functions are distinct, the 1931 2° function z stands out: it has a lower value at short wavelength, i.e. in the range 400-430 nm, whereas the other three z functions are nearly identical in the range 400-430 nm. Form this, it can be expected that the three other CMFs (namely 1964 10°, 2005 2°, 2005 10°) will yield chromaticity predictions that tend to agree with each other, especially when an SPD has a large amount of short-wavelength light, and which will disagree with chromaticities calculated using the 1931 2° CMFs. Accordingly, in some embodiments, either of these three CMFs can be used to target a chromaticity and obtain a perceptually-white SPD. Alternately, a suitable CMF for some embodiments may be a CMF whose z function has a value in the range 0.15-0.25 at 405 nm (in contrast to the 1931 2° CMF z, which has a value of about 0.1).

While the existence of various CMFs is known in the art, color targeting is customarily achieved with the 1931 2° CMFs. The prior art considers this suitable, failing to realize that the differences in CMF predictions are exacerbated, for instance, in the case of an SPD having a large fraction of violet light. Some embodiments of the invention are characterized by SPDs having a large discrepancy between their chromaticity according to 1931 2° CMFs and other CMFs.

Figure 18A:
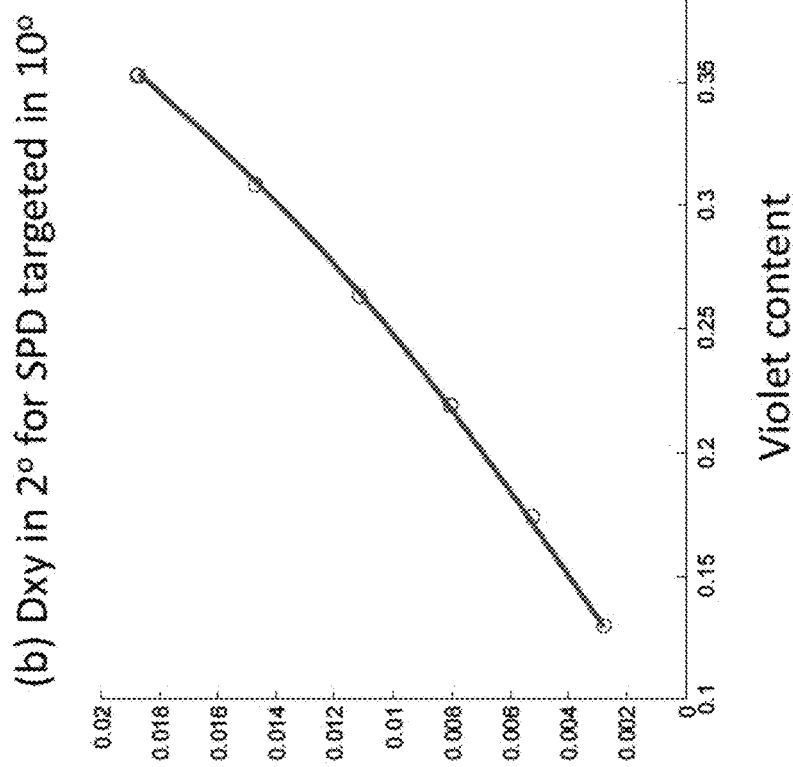
FIGS. 18a-18b illustrate spectral power distributions having varying violet contents according to one or more embodiments of the invention.
Figure 18B:
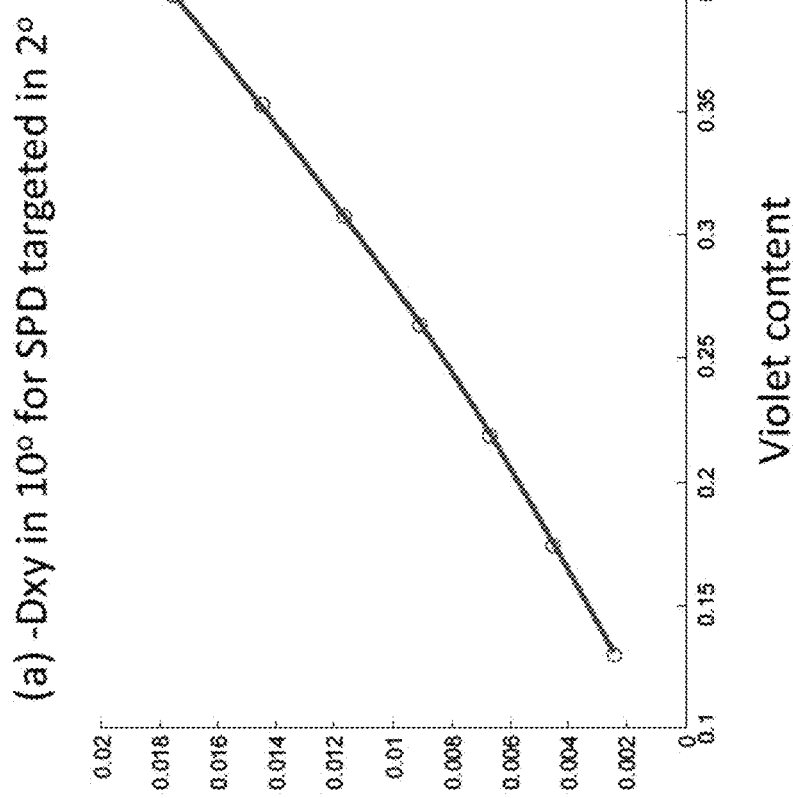

FIG. 18a illustrates SPDs having varying violet contents (in the range 390-420 nm) which have been targeted on-Planckian at 4000 K with 2° CMFs, and shows their distance from Planckian Dxy calculated with 10° CMFs. As the violet content increases, Dxy increases, showing that "nominally" targeted SPDs are off-color according to the 10° CMF calculation (Dxy is negative, so a pinkish tint is predicted) and that this effect becomes significant for violet contents above 15%. For prior art SPDs having very low violet contents, the discrepancy between CMFs may be tolerable, while it may be problematic for SPDs with a high violet content. FIG. 18(b) shows the converse situation where the SPD is targeted with 10° CMFs and Dxy is calculated with 2° CMFs. The conclusions are the same: an SPD with large violet content (more than 15% or 20% or 25% or 30%) has a large discrepancy, and may appear off-color according to 2° CMFs (Dxy is positive, so a greenish tint is predicted) while it is properly targeted according to 10° CMFs.

Accordingly, some embodiments have a violet content, a Dxy (calculated with 1931 2° CMFs), and a Dxy (calculated by other CMFs, such as the 1964 10° CMFs), which are given by the table below:

| Violet content > | Dxy (2°) > | Dxy (other) < |
|---|---|---|
| 15% | 3E−03 | 1E−03 |
| 20% | 5E−03 | 1E−03 |
| 25% | 7E−03 | 1E−03 |
| 30% | 1E−02 | 1E−03 |
| 35% | 1E−02 | 1E−03 |

FIGS. 6a-6d illustrate targeting by various CMFs. FIG. 6a is an SPD at 3500K, on-Planckian according to 2° CMFs. FIG. 6b is an SPD at 3500K, on-Planckian according to 10° CMFs. FIG. 6c is the (x-y) color space calculated with 2° CMFs, with the SPD of FIG. 6a shown as a square and the SPD of FIG. 6b shown as a circle. FIG. 6d is the (x-y) color space calculated with 10° CMFs, with the SPD of FIG. 6a shown as a square and the SPD of FIG. 6b shown as a circle. In both FIGS. 6c and 6d the black curve is the Planckian locus. SPD. 6a is on-Planckian on FIG. 6c whereas SPD 6b is off-Planckian, and vice-versa in FIG. 6d. In FIG. 6d, SPD 6a is off-Planckian by a very large amount, indicating a very large pink tint.

Therefore it appears that using the 2° CMFs for color targeting may not be desirable, especially in some cases where the spectrum has a lot of violet light. To obtain a perceptual match (for instance, to a Blackbody radiator at a given CCT), it may be advantageous to use the 10° CMFs, or other accurate CMFs. The development of improved CMFs is an ongoing process. Embodiments can make various uses of improved CMFs.

As illustrated in FIGS. 6a-6d, the distinction between various CMFs can be expressed as follows. Consider a chromaticity specification (or test), expressed as a target center chromaticity (for instance, on the Planckian locus) and a tolerance such as a maximum distance from the target point (calculated for instance as a Cartesian distance in a color space such as (uv), (u'v'), (xy)). As shown in FIG. 6, an SPD may meet the specification according to a set of CMFs but not another. For instance on FIG. 6b, the SPD is within a distance Dxy=<0.03 of the Planckian (and also Dxy=<0.025, 0.02, 0.015, 0.01, 0.005) according to the 10° CMFs [FIG. 6(d)]; on the other the same SPD is above a distance Dxy>=0.03 of the Planckian (and also Dxy>=0.025, 0.02, 0.015, 0.01, 0.005) according to the 2° CMFs [FIG. 6(d)]. Accordingly, some embodiments meet a chromaticity specification according to desired CMFs (such as the 1964 10° CMFs) but not according to the 1931 2° CMFs.

Likewise, as shown in FIGS. 6a-6d, some embodiments have SPDs which are substantially off-Planckian according to the 2° CMFs but on-Planckian according to more desirable CMFs (including the 10° CMFs). Further, FIG. 6c indicates that the SPD of FIG. 6b is substantially off-Planckian, whereas FIG. 6d indicates that the SPD if FIG. 6b is substantially on-Planckian.

In some embodiments, SPDs have a distance to the Planckian locus that is smaller when it is computed with 10°

CMFs than when it is computed with 2° CMFs—as is the case for the SPD on FIG. 6d.

It should be appreciated that these considerations about the difference in chromaticity (between different sets of CMFs) can be especially meaningful for an SPD having large amounts of violet radiation, as is the case of some embodiments, and as illustrated above.

While the above discussion focuses on SPDs targeted on-Planckian, off-Planckian targeting is also possible. In some embodiments, for an SPD which is perceptually slightly pinkish (corresponding to a slightly below-Planckian targeting) to be preferred. In such cases, the same aspects are valid: given a desired chromaticity, the SPD may be targeted using non-2° CMFs different from the 1931 2° CMFs, and the chromaticity distance to the desired target may be larger according to 2° CMFs than to the non-2° CMFs.

Chromaticity distances may be expressed in a variety of color spaces like (xy) and (uv), and values can be converted between these. For instance, referring to FIG. 6, the SPD of (b) is separated from the Planckian locus (according to 2° CMFs) by about Dxy=0.030 and Duv=0.015, according to the conversion factor discussed earlier.

Figure 7:
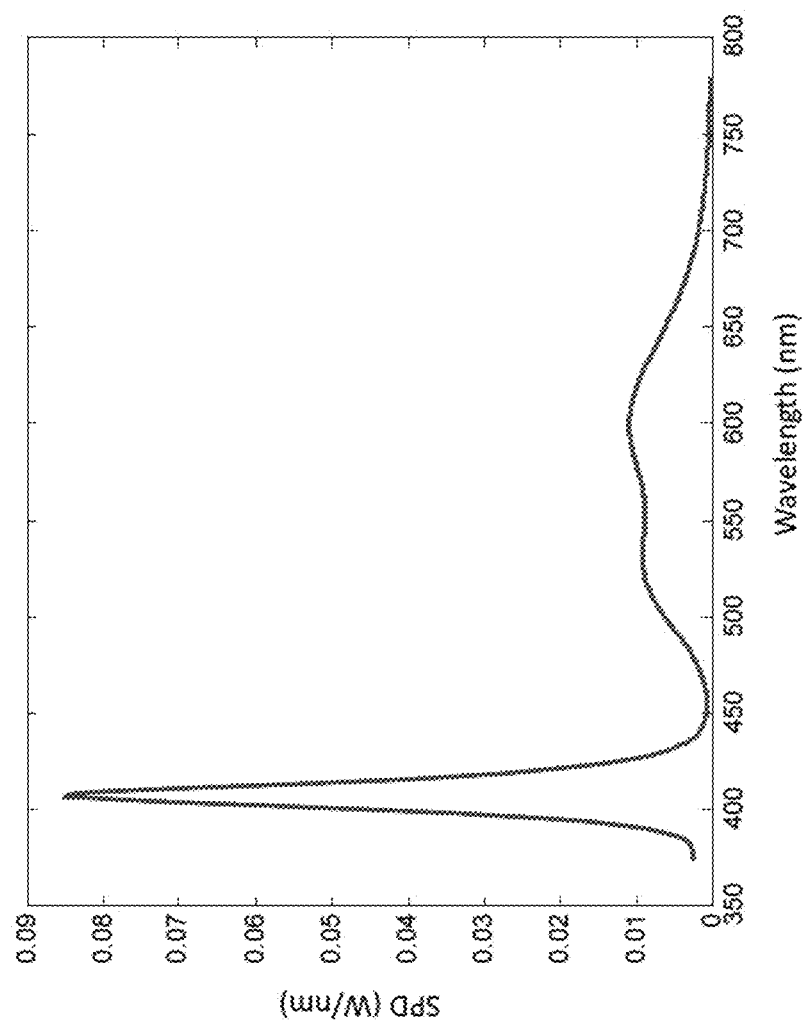
FIGS. 7-8 illustrate the spectral power distributions according to one or more embodiments of the invention.

FIG. 7 is an experimental measurement of an embodiment, illustrating 10° targeting. This spectrum has a CCT of 4000K, a CRI Ra>80, and is on-Planckian according to the 1964 10° CMFs. It uses a 405 nm LED and the following phosphors: (Ba,Sr)2SiO4:Eu (BSS) and (SrxCa1-x)AlSiN3: Eu (SCASN).

In many embodiments, it may be necessary to use appropriate CMFs to create embodiments with the intended chromaticity perception. Alternately, embodiments may be obtained by aid from perceptual experiments rather than from calculations of chromaticity. In some cases, a spectrum is obtained by matching the perceived chromaticity of another light source (for instance, a filament lamp of a desired CCT or another light source like a ceramic metal halide source, which may be on- or off-Planckian). This process may be accomplished by selecting an existing light source, determining its chromaticity with CMFs which are different from the 1931 2° CMFs, and matching this chromaticity, according to the same CMFs, with an embodiment. Alternatively, the match may be achieved by a visual match, where the embodiment's spectrum is configured such than a human subject considers the two perceived chromaticities as substantially similar or identical.

Although the present examples are on-Planckian, slight deviations from a desired chromaticity are acceptable. For example, an embodiment may be within a chromaticity Duv distance less than 6E-3 (or 4E-3, or 2E-3, or 1E-3) from the Planckian locus. This Duv distance may be calculated with 1964 10° CMFs.

Some embodiments of the invention are lighting systems emitting a spectrum taught herein. Such systems may be lamps or fixtures or displays. They may comprise optical elements. For instance, a lamp may comprise an optic (directional or diffuse), a fixture may comprise a waveguide. Some embodiments take into account the transmission of such optical elements, such that the chromaticity of interest is obtained for the final light emitted by the system. For instance, if a lamp uses an optic which absorbs some violet light, the lamp may comprise an LED source having a slightly off-chromaticity SPD (with an excess of violet) to compensate for said absorption, such that the final emitted SPD is on-chromaticity.

In some embodiments, care is taken to use optical elements having low violet absorption. For instance, PMMA, PMMI or glass may be preferred materials. In some embodiments, less than 10% (or 5%, 2%, 1%) of the light emitted by the light-emitter is absorbed in the optical elements.

In some embodiments, care is taken to avoid the use of materials containing fluorescent whitening agents, which can unwantedly absorb violet light and fluoresce blue light.

Color Rendition

Besides chromaticity, embodiments are distinguished by their color rendition. One may expect that, with a large blue spectral gap, color renditions (such as CRI Ra or R9) may be very poor. However, it was discovered that it was possible to obtain unexpectedly high values of Ra and R9. In particular, use of a long-wavelength red phosphor substantially improved R9.

Some embodiments have a large violet fraction while maintaining Ra>80 and R9>0. Based on our discovery, a series of spectra which met these criteria were generated by combining the spectrum of a violet pump LED at 405 nm with the spectra of green and red phosphor having various peak wavelengths.

Figure 8:
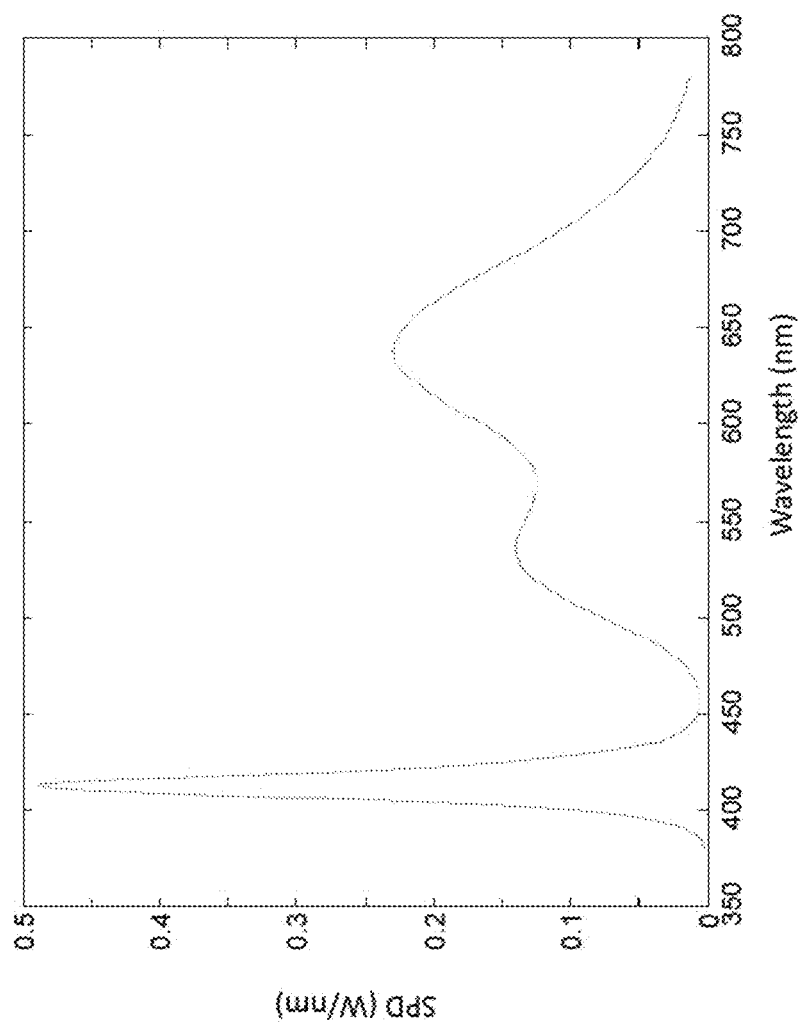

FIG. 8 shows an experimental embodiment with a CCT of 3000 K, Ra=85, R9=85, and a violet fraction of 16%. This spectrum uses a violet LED, a 524-silicate green phosphor and a 650-CASN red nitride phosphor.

Figure 9:
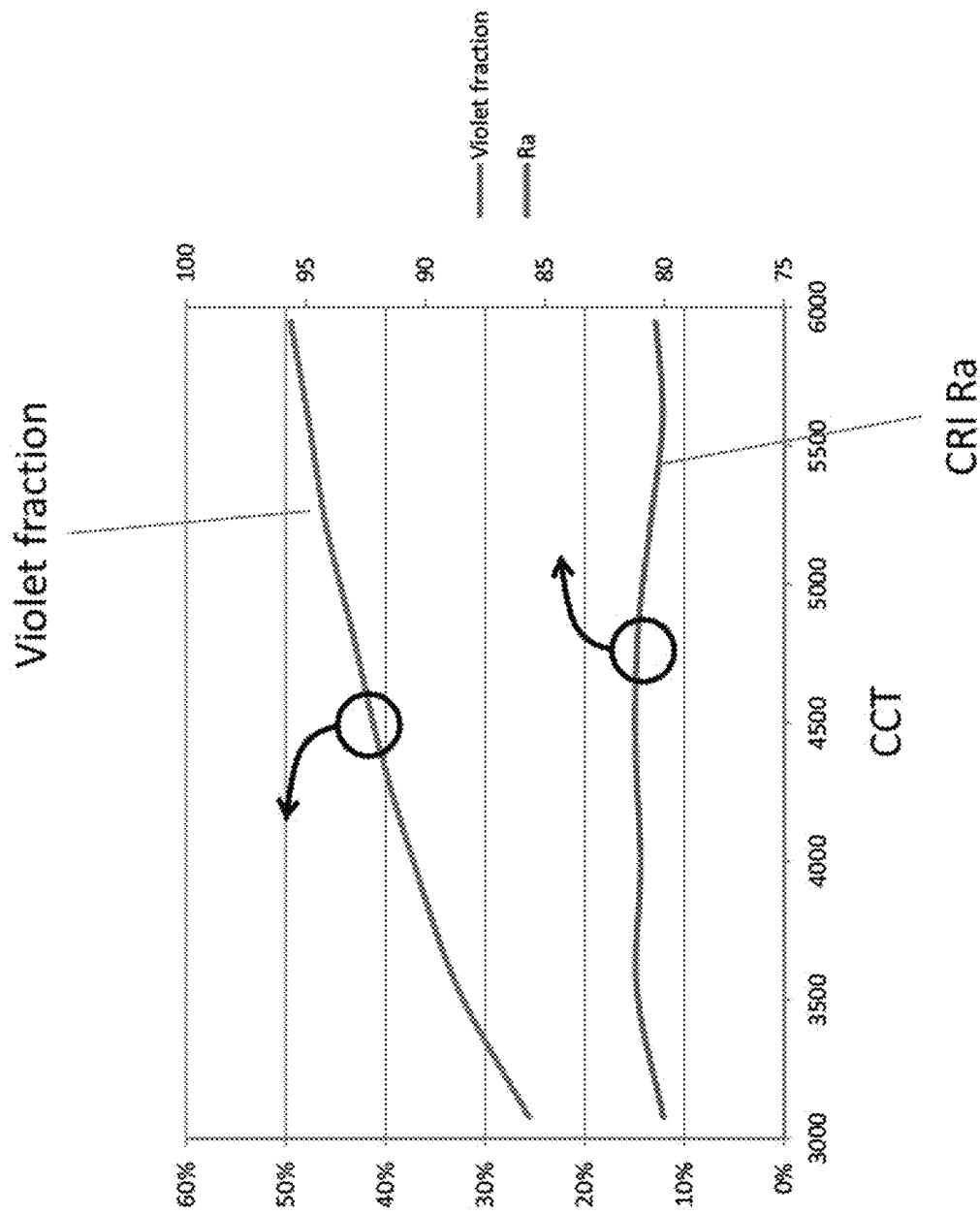
FIGS. 9-11 illustrate color metrics versus correlated color temperature according to one or more embodiments of the invention.

FIG. 9 shows color metrics versus CCT for a series of embodiments, all on-Planckian with 10° CMFs. The corresponding SPDs have been configured to maximize their violet fraction while keeping Ra>80. However, by using a slightly different violet emitter (such as a laser) and other phosphors, even higher violet fractions can be envisioned. The examples shown here are merely illustrative of possible values, and their optimization is of course possible. In general, as CCT increases, the maximum violet fraction increases.

It is possible to reach even higher values of color rendition. Accordingly, some embodiments have a large violet fraction while maintaining Ra>90 and R9>90.

Figure 10:
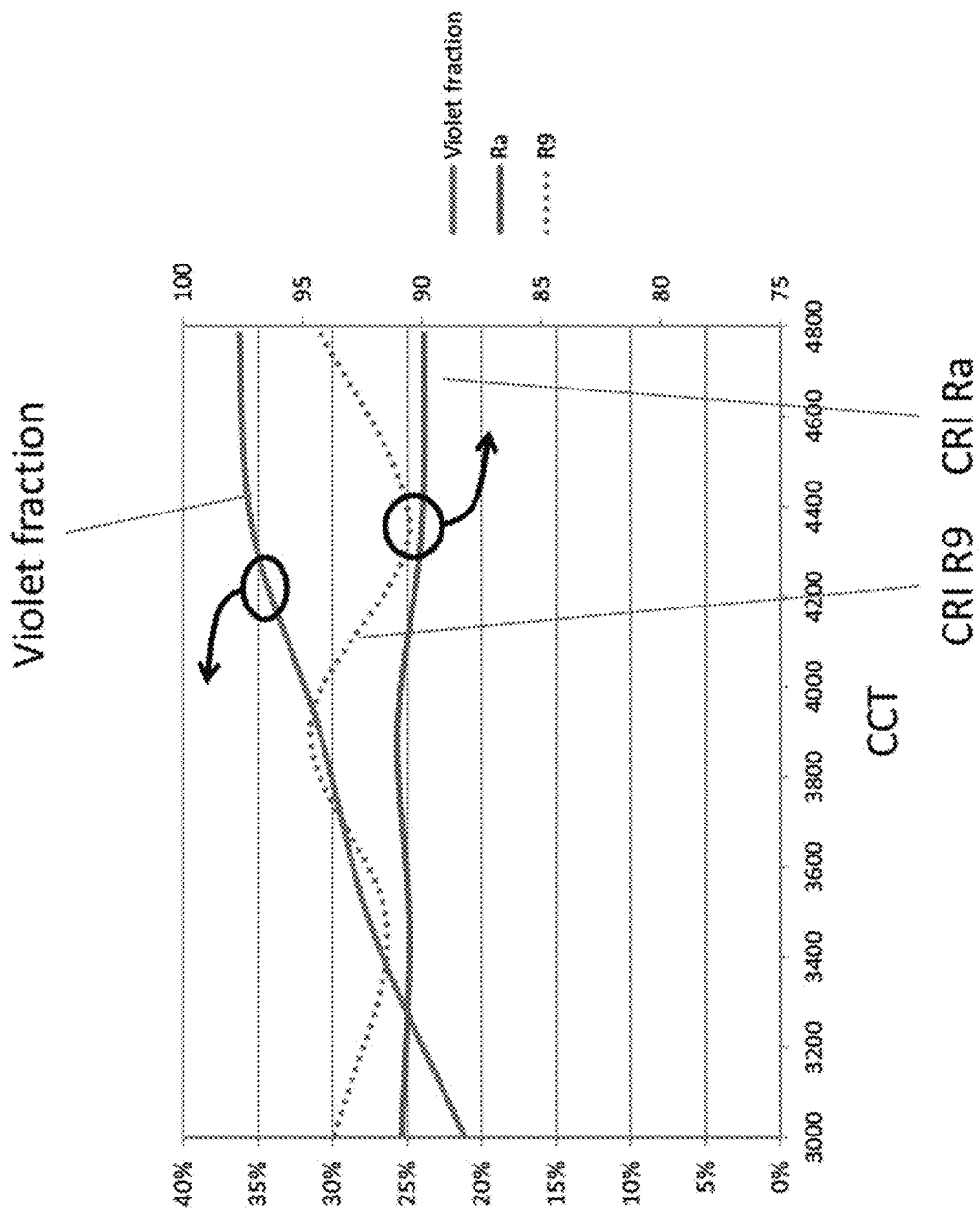

FIG. 10 shows color metrics versus CCT for another series of embodiments, all on-Planckian with 10° CMFs. These demonstrate R9>90 and Ra>90. Similar comments apply as to those of FIG. 9.

Even higher values of color rendition are also possible, for instance R9=95. Besides, embodiments can reach a high value of the TM-30 red rendering metric Rfh1 (e.g. Rfh1>50 or 80 or 90 or higher).

Some embodiments have applications in the medical field. In hospitals, the quality of light is sometimes evaluated using the COI index which is indicative of the color rendition of skin with various hemoglobin levels. In particular, some standards require that lamps in hospitals have a specific range of CCT and COI. To comply with AS 1680.2.5 requirements for the reliable diagnosis of cyanosis, the COI should be 3.3 or lower and the lamp correlated color temperature should be between 3300 K and 5500 K. Embodiments of the invention meet these targets while also providing a high violet fraction.

Figure 11:
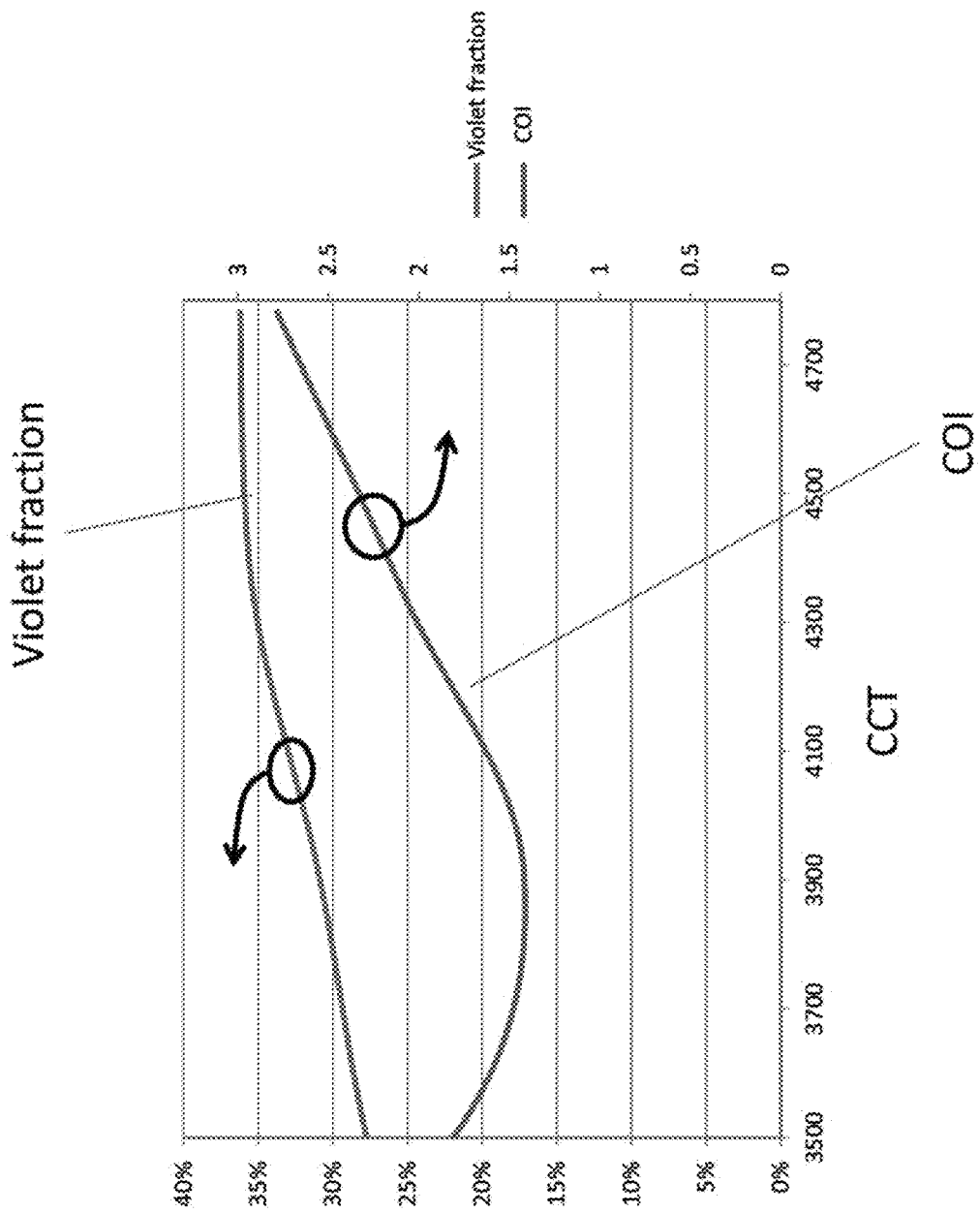

FIG. 11 illustrates embodiments having a CCT in the range 3500-4800K and a COI below 3, together with a high violet fraction in the range 25%-40%.

Figure 12:
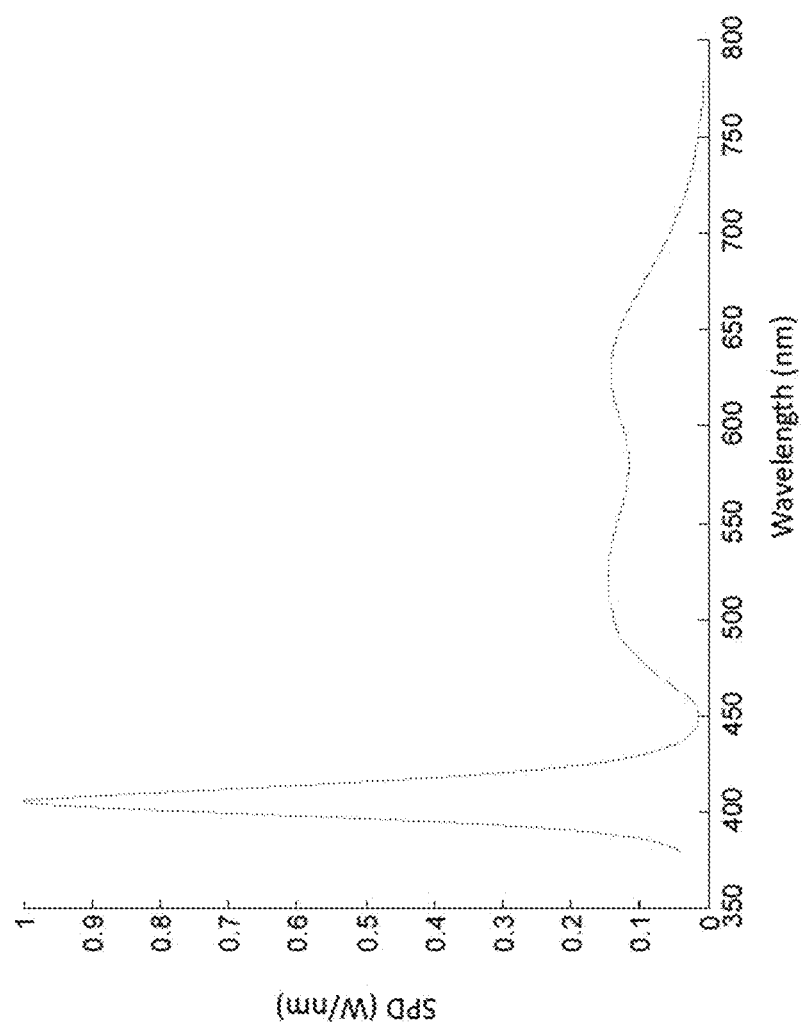
FIG. 12 illustrates the spectral power distribution according to one or more embodiments of the invention.

A specific example of such a spectrum is shown on FIG. 12. This spectrum has the same chromaticity as a 5000 K Blackbody (calculated with 10° CMFs). Its CCT (calculated with the conventional calculation, based on 2° CMFs) is 4800 K. It has Ra>90, R9>95, COI=2.7, Rf=70, Rfh1=80, and a violet fraction of 36%. The spectra whose color metrics are shown on FIGS. 10-11 are similar to this spectrum, with slight variations in the intensity and peak position of the phosphors to match various CCTs.

This violet content can also be expressed in terms of violet watts (in the range 390-420 nm) per lumen of light: the spectrum has 2 mW/lm of violet light. This value is high compared to a conventional light source. A blackbody at 5000 K has 0.3 mW/lm of violet light.

At other CCTs, other embodiments are also distinguished by a high ratio of violet mW to lumens. This is illustrated on FIG. 13.

Figure 13:
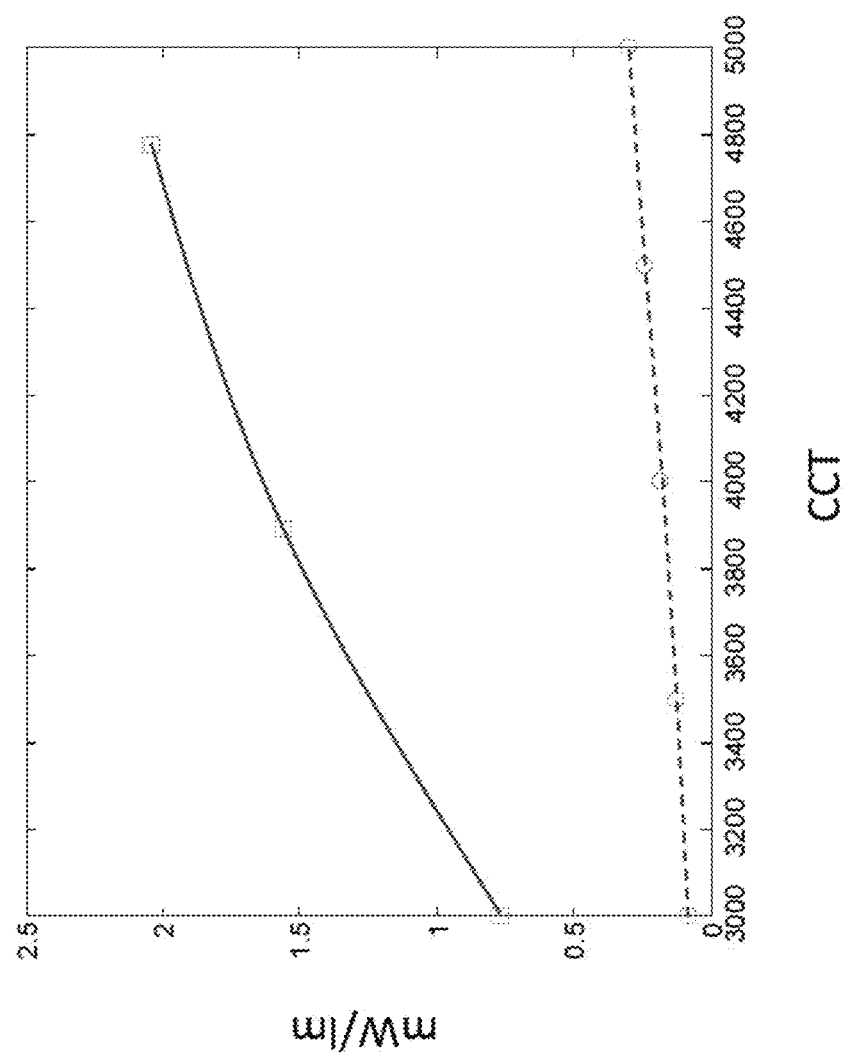
FIG. 13 illustrates the violet content as related to correlated color temperature according to one or more embodiments of the invention.

FIG. 13 shows mW/lm (where the mW are the total violet watts computed in the range 390-420 nm) for sources at various CCTs. The dashed line shows Blackbody radiators. They all have a low mW/lm, always less than 0.4. The full line shows embodiments of the invention (the corresponding spectra are the same which underlie FIGS. 10 and 11). These embodiments are all on-Planckian (with 10° CMFs), with Ra>90 and R9>90. They are distinguished by high mW/lm, always above 0.5 (and even above 0.7). For CCTs in the range 3500-5000 K (which is relevant for medical applications), these embodiments have more than 1 mW/lm. In general, the embodiments of FIG. 13 have more than 5 times the amount of violet mW/lm than does a Blackbody radiator at the same CCT.

Further, although no standard blue-based white LEDs are shown on FIG. 13, they would have a much smaller violet mW/lm figure-of-merit than even Blackbody sources, since they hardly contain any violet light. For instance a typical blue-based white LED at 3000 K has less than 0.01 mW/lm of violet light.

As has previously been mentioned, different violet ranges (or even weighing by a violet bactericidal action spectrum) can be envisioned. This will change the values mentioned above, but will not change the general trend that embodiments have much higher violet mW/lm that standard light sources.

Light Levels

Expressing the violet content in mW/lm enables one to predict the dose of violet light in a given application. For instance, if a light source having a violet content of 1 mW/lm emits 1000 lm and illuminates a surface of 1 square meter (i.e., the source has an illuminance of 1000 lux), the violet flux is 1 W/m2.

In various embodiments, light sources emit about 1000 lm (or 500 lm, 1500 lm, 2000 lm, etc . . . ) of light. They have violet contents in the range 0.5-3 mW/lm. Further, they may illuminate an area of about 0.1 m2 to 1 m2 to 3 m2 (for instance, by placing a 10-degree beam source at a distance of less-than-one meter to a few meters from the illuminated surface). Depending on these configurations, a variety of violet W/m2 can be achieved as needed for bactericidal effects.

Table 1 below shows a few examples, for a light source emitting 1000 lm. In this case, the violet irradiance ranges from about 0.17 W/m2 to 30 W/m2.

| lm | violet mW/lm | spot area (m$^2$) | violet W/m$^2$ |
|---|---|---|---|
| 1000 | 0.5 | 0.1 | 5 |
| 1000 | 0.5 | 1 | 0.5 |
| 1000 | 0.5 | 3 | 0.17 |
| 1000 | 1 | 0.1 | 10 |
| 1000 | 1 | 1 | 1 |
| 1000 | 1 | 3 | 0.33 |
| 1000 | 2 | 0.1 | 20 |
| 1000 | 2 | 1 | 2 |
| 1000 | 2 | 3 | 0.67 |
| 1000 | 3 | 0.1 | 30 |
| 1000 | 3 | 1 | 3 |
| 1000 | 3 | 3 | 1 |

By increasing the source lm, higher values can be achieved, for instance 100 W/m2.

In various embodiments, the source illuminates a surface with a violet irradiance of at least 0.5 W/m2 (or 1, 2, 5, 10, 20, 50, 100 W/m2). In some embodiments, the violet irradiance is in the range 1-50 W/m2 or in the range 1-10 W/m2.

Some embodiments are methods of using a source described in this application, where the method comprises illuminating a surface for bactericidal effects with a selected violet irradiance. The method may comprise suppressing a bacterial population with a selected suppression rate.

As mentioned above, a common goal of LED lighting is to increase LER. One skilled in the art of LED lighting would typically not design an LED whose spectrum has such a large amount of violet light. Indeed, the human eye is much less sensitive to violet light than it is to blue light. As a result, when the amount of violet light in a spectrum is increased, the luminous efficacy of radiation (LER) of the resulting spectrum decreases. FIG. 17 shows the LER of a variety of LED spectra versus violet fraction (in the range 390-420 nm). As the violet fraction is increased, the LER decreases from 337 lm/W (for 0.5% violet in the SPD) to 257 lm/W (for 25% violet light in the SPD). FIG. 17 shows that by varying the amount of violet and blue radiation a desired chromaticity and violet fraction can be achieved.

Dynamic Mode

In some embodiments emitted SPD may vary. In one or more embodiments, a lighting system comprises a first source which emits pure violet light and a second source which emits a spectrum having green and red light. The latter source may be a violet-pumped LED with a green and a red phosphor, but with a small violet fraction.

Such dynamic embodiments (where the spectrum can be modified or tuned) may be formed using the teachings of U.S. patent application Ser. No. 14/531,545. This includes multiple emitters including LEDs at various wavelengths (including violet LEDs) and phosphors, whose power may be varied to modify a spectrum.

When the two light sources are on, the system emits white light with a desired chromaticity (for instance, on-Planckian with 10° CMFs). When only the violet source is on, the system only emits violet light. The first mode may be used when users are present and/or at a predetermined time; the second mode may be used for disinfection/bactericidal effects only, when no user is present in the room and/or at a predetermined time. This reduces the energy consumption of the system, by only providing the bactericidal effect. For instance, in a system whose violet fraction is 50% (in white-light mode), the energy consumption may be about halved when only the violet emitters are present.

In various embodiments, a switch between the white-light mode and the violet-only mode may be triggered by a variety of factors including: presence/movement detectors, time of day, computer algorithms based on machine learning to infer the presence of a user, and other methods known in the art of dynamic lighting.

Figure 14:
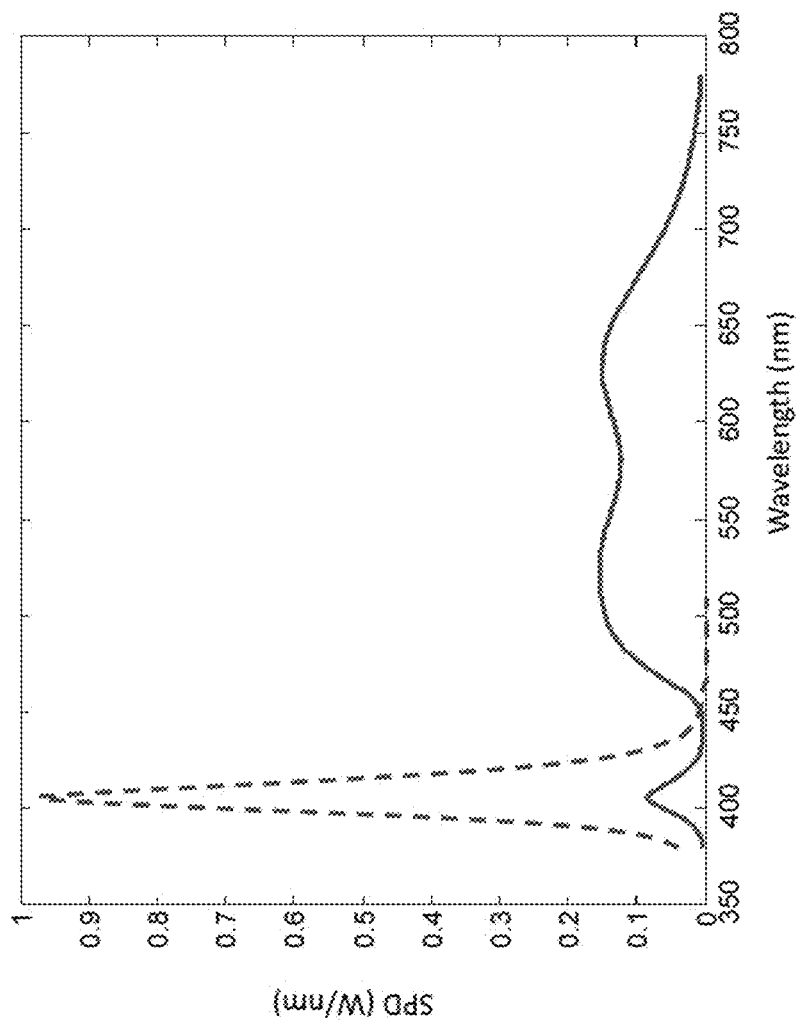
FIG. 14 illustrates a spectrum corresponding to the combination of one or more types of LEDs according to one or more embodiments of the invention.

FIG. 14 shows how the spectrum of FIG. 12 can be obtained by combining a direct violet LED spectrum (dashed line) with a second spectrum having a violet pump LED, a green phosphor and a red phosphor (full line). In this example, the second spectrum is not white—it is significantly above-Planckian; the combination of this spectrum with the violet spectrum yields the spectrum of FIG. 12 which is on-Planckian (when calculated with 10° CMFs).

In other embodiments, the two light sources are substantially white but have differing violet contents. Teachings of this invention can be used to match the chromaticity of the two sources.

Emitters Selection

In various embodiments, a light source includes one or more violet pump LEDs, as well as LEDs at other wavelengths (for instance blue, green, red), and phosphor materials emitting at various wavelengths (including blue, green, red). In some embodiments, the violet pump LEDs are combined with LEDs emitting at a longer wavelength (various combinations can be used, for instance, violet LED pumping phosphor plus direct blue LEDs, or direct violet LEDs plus blue LEDs pumping phosphors, or violet LEDs pumping phosphors and blue LEDs pumping phosphors). In one or more embodiments, a light source only includes violet pump LEDs that are configured to pump phosphors. U.S. patent application Ser. No. 14/531,545 discloses various systems and methods for combining LEDS and is herein incorporated by reference.

In one embodiment, a light source may include a violet pump emitter and phosphors. The emission peak wavelength for the pump may be in the range 400-410 nm, or in the range 403-407 nm. The pump may be an LED or laser diode. This embodiment may be advantageous in some cases. For instance, use of only one type of light source (only violet LEDs for instance) means that the driving electronics are simple: standard one-stage drivers can be used to drive the light sources. This enables a cheap and robust system. The reliability is controlled by the reliability of the violet LEDs, so that drift of chromaticity over time may be good. Further, if very-efficient violet LEDs are used, this may provide an efficient configuration. If the phosphors are present over all the violet LEDs, the light source may have a color-uniform appearance when powered, which can reduce the need for color mixing in a lighting system.

In other embodiments, a light source may include a violet emitter and a blue (or cyan or green) emitter, and some phosphors. The phosphors may be pumped by the violet LED and/or the blue LED. This embodiment may be advantageous in some cases. It may enable a tunable light source, where the power feeding the violet emitter and the blue emitter are varied to modify the emitted spectrum. The blue LED may pump all the phosphors, which may minimize the Stokes shift and provide high efficiency. The violet LED may by a highly-efficient LED, which is suited to pump some or all the phosphors. The light source may be configured to have a desired white chromaticity at a given ratio of electrical powers driving the violet and blue LEDs.

Further, a light source may include two sub-sources: a violet emitter with a first set of phosphors (source 1) and a blue emitter with a second set of phosphors (source 2). This embodiment may be advantageous in some cases. For instance, the chromaticities of source 1 and source 2 may be identical or substantially similar. In this case, the light source may be tuned between the two sources without the user noticing a change in chromaticity. This may enable a seamless switch from bactericidal mode to standard lighting mode (which may be more energy-efficient). The teachings of this invention may help ensure that both sources have a perpetually-similar chromaticity, for instance because they are color-targeted with an adequate set of CMFs.

In one embodiment, a light source may include a first phosphor emitting substantially green (or green-cyan-yellow) light and a second phosphor emitting substantially red (or orange-red-infrared) light.

Suitable classes of first phosphors with an emission peak between 500 nm and 550 nm include silicates or fluorosilicates doped with Eu2+; chalcogenides doped with Eu2+; nitridosilicates, oxynitridosilicates, oxynitridoaluminosilicates or beta-sialons doped with Eu2+ and carbidooxynitridosilicates doped with Eu2+. Specific non-limiting examples of suitable first phosphors include:

$(Ba,Sr)_2SiO_4:Eu^{2+}$ (a typical formulation of "BOSE")
$(Mg,Ca,Sr,Ba,Zn)_2SiO_4:Eu^{2+}$ (a broader formulation of "BOSE")
$(Sr,Ca,Ba)(Al,Ga)_2S_4:Eu^{2+}$
$Eu_x(A1)_{6-z}(A2)_zO_yN_{8-z}(A3)_{2(x+z-y)}$, where $0 \leq z \leq 4.2$; $0 \leq y \leq z$; $0 < x \leq 0.1$; A1 is Si, C, Ge, and/or Sn; A2 is Al, B, Ga, and/or In; A3 is F, Cl, Br, and/or I
$M(II)_{1-x-z}M(I)_zM(III)_{x-xy-z}Si_{1-x+xy+z}N_{2-x-xy-2w/3}C_{xy}O_{w-v/2}H_v:A$ and
$M(II)_{1-x-z}(M(I)_zM(III)_{x-xy-z}Si_{1-x+xy+z}N_{2-x-xy-2w/3-v/3}C_{xy}O_wH_v:A$,
wherein $0<x<1$, $0<y<1$, $0 \leq z<1$, $0 \leq v<1$, $0<w<1$, $x+z<1$, $x>xy+z$, and $0<x-xy-z<1$, M(II) is at least one divalent cation, M(I) is at least one monovalent cation, M(III) is at least one trivalent cation. H is at least one monovalent anion, and A is a luminescence activator doped in the crystal structure.

Suitable classes of second phosphors with an emission peak between 600 nm and 670 nm include nitridosilicates doped with Eu2+; carbidonitridosilicates doped at least with Eu2+; chalcogenides doped with Eu2+ and oxides, oxyfluorides or complex fluorides doped with Mn4+. Specific non-limiting examples of suitable second phosphors include:

$(Sr,Ca)AlSiN_3:Eu^{2+}$ (a typical formulation of "SCASN")
$(Ba,Sr,Ca,Mg)AlSiN_3:Eu^{2+}$ (a broader formulation of "SCASN")
$(Ba,Sr,Ca,Mg)_xSi_yN_z:Eu^{2+}$ (where $2x+4y=3z$)
The group:

$$Ca_{1-x}Al_{x-xy}Si_{1-x+xy}N_{2-x-xy}C_{xy}:A \qquad (1);$$

$$Ca_{1-x-z}Na_zM(III)_{x-xy-z}Si_{1-x+xy+z}N_{2-x-xy}C_{xy}:A \qquad (2)$$

$$M(II)_{1-x-z}M(I)_zM(III)_{x-xy-z}Si_{1-x+xy+z}N_{2-x-xy}C_{xy}:A \qquad (3)$$

wherein $0<x<1$, $0<y<1$, $0 \leq z<1$, $0 \leq v<1$, $0<w<1$, $x+z<1$, $x>xy+z$, and $0<x-xy-z<1$, M(II) is at least one divalent cation, M(I) is at least one monovalent cation, M(III) is at least one trivalent cation. H is at least one monovalent anion, and A is a luminescence activator doped in the crystal structure.

$(Na,K,Rb,Cs)_2[(Si,Ge,Ti,Zr,Hf,Sn)F_6]:Mn^{4+}$
$(Mg,Ca,Zr,Ba,Zn)[(Si,Ge,Ti,Zr,Hf,Sn)F_6]:Mn^{4+}$
$(Mg,Ca,Sr,Ba)(S,Se):Eu^{2+}$
$(Na,K,Rb,Cs)_2[(Si,Ge,Ti,Zr,Hf,Sn)F_6]:Mn^{4+}$ (Mg,Ca,Zr,Ba,Zn) [(Si,Ge,Ti,Zr,Hf,Sn)F$_6$]:Mn$^{4+}$
3.5MgO.0.5MgF$_2$.GeO$_2$:Mn$^{4+}$
Sr[LiAl$_3$N$_4$]:Eu$^{2+}$.

Embodiments may make use of a first phosphor with an emission peak between 500 nm and 550 nm and a second phosphor with an emission peak between 600 nm and 670 nm. Optionally, one or more additional phosphor(s) may be used as needed to optimize the luminous flux or the color rendering properties of the LED. The additional phosphor(s) may have an emission peak between 500 nm and 670 nm, or between 550 nm and 600 nm. Examples of suitable classes of additional phosphors include those of the aforementioned first and second phosphors classes emitting at different peak wavelengths than the specific first and second phosphors selected, plus garnets doped with Ce$^{3+}$, nitrides doped with Ce$^{3+}$ and alpha-sialons doped with Eu$^{2+}$. Some specific non-limiting examples of such additional phosphors include:

(Y,Gd,Tb,La,Sm,Pr,Lu)$_3$(Sc,Al,Ga)$_5$O$_{12}$:Ce$^{3+}$
(La,Y,Lu)$_3$Si$_6$N$_{11}$:Ce$^{3+}$
(Lu,Ca,Li,Mg,Y) alpha-SiAlON doped with Eu$^{2+}$ and/or Ce$^{3+}$ Alternatively, the phosphors can be layered sequentially in layers or laid out in a parallel fashion (e.g. in a pattern of small patches) around the LED pump, as also known in the art.

One skilled in the art will know how to select phosphors with the proper peak wavelengths, and adjust the amount of each phosphor in the phosphor blends, layers or patterns in order to target any given color point of interest, obtainable per the color mixing rule as long as it lies within the region subtended by the color points of each phosphor and the LED pump in the CIE chromaticity diagram. Achieving LED spectra with good color rendering properties is however not straightforward since the influences of different spectral components are highly non-linear, and there are no simple rules but rather an element of art involved in obtaining desirable Ra and R9 values, for example. It is traditionally assumed in the lighting industry that a white spectrum with good color rendering for general lighting purposes (e.g. with a CRI value of 80 or higher and an R9 value higher than 0) should have a substantial emission in the blue wavelength region, especially for CCT values above 2500K. For instance, it has been first predicted by numerical modeling and later demonstrated experimentally that SPDs with peaks around 450 nm, 540 nm and 610 nm provide a CRI of 80 or greater when color-balanced on the Planckian locus across the range of CCT values used in general lighting. As a consequence, the tri-phosphor fluorescent lamp technology was developed based on those specific emission peak wavelengths. Since a white bactericidal spectrum with chromaticity on or substantially on the Planckian locus may need to have its emission between 440 nm and 480 nm reduced or suppressed, a related impact on the CRI value from this spectral deficiency around the 450 nm wavelength (widely considered critical to CRI based on the aforementioned precedents) can be reasonably expected in comparison to typical white blue-pumped LEDs containing the same green and red phosphors or white violet-pumped LEDs containing a blue-emitting phosphor and the same green and red phosphors. Unexpectedly, we were able to obtain white bactericidal LEDs exhibiting a local minimum in their spectral power distribution (SPD) between 420 nm and 500 nm and color-balanced near the Planckian locus with both Ra≥80 and R9≥0, and higher values, as shown in the examples given herein.

The lighting apparatus disclosed here can be an LED package or module, a solid state lamp (including direct replacement lamps for incandescent, halogen or fluorescent lamps), solid state lighting ("SSL") fixture, light engine (the light generating component of a fixture), backlighting unit etc. Whenever the word "LED" is used in the foregoing specification, it is only meant as a generic example of such a lighting apparatus not limiting the scope of applicability of this invention.

An optional band-stop filter (also known as a notch filter) can be added to the lighting apparatus described above, to suppress the blue part of the spectrum even further if necessary. Such filters are known in the art and can be custom ordered from a variety of commercial suppliers.

Bactericidal Effect

Figure 15:
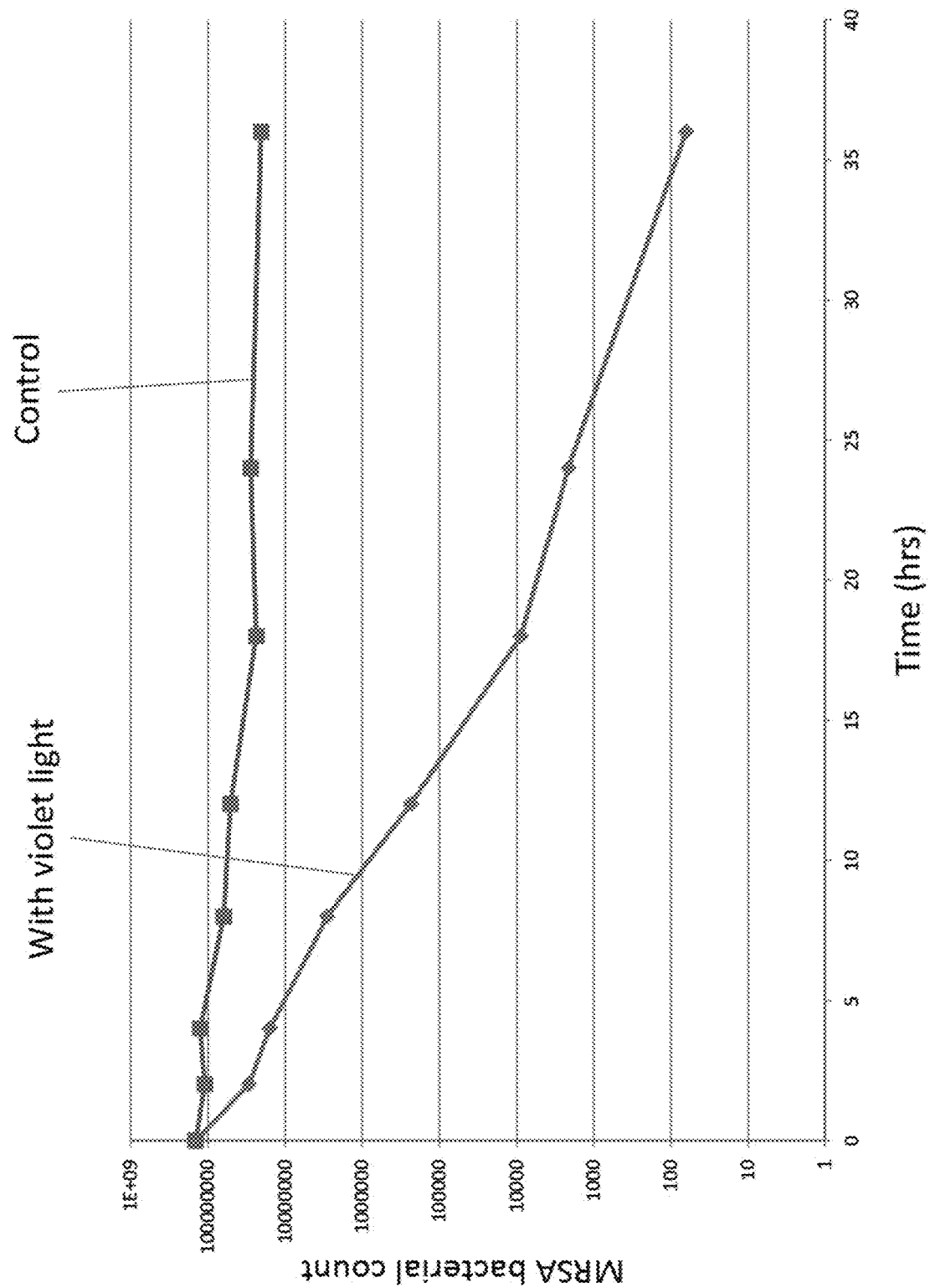
FIG. 15 illustrates experimental results of violet light on bacteria according to one or more embodiments of the invention.

FIG. 15 shows experimental results of violet light on bacteria. FIG. 15 shows the bacterial count of MRSA bacteria, cultured and deposited on a glass slide, over time. In the absence of light ("Control") there is a mild bacterial reduction with time due to natural bacterial death in this medium (the drop is less than a factor of ten in 36 hrs). The experimental LED light source emits violet light peaking at 405 nm, and provides a violet irradiance on the order of 5-10 W/m2 on the glass slides. In the presence of this violet light, very significant bacterial reduction is observed.

A fit of the bacterial suppression yields a population rate P=10^(hrs/5). Therefore, there is 90% suppression (i.e. suppression by a factor of ten) in about five hours and 99% suppression (i.e. suppression by a factor of a hundred) in about ten hours.

Some embodiments provide suppression (or kill rate) of a bacterial population of at least a factor of ten in a given amount of time, for instance 1 hr, 2 hr, 4 hr, 10 hr, 12 hr.

Some embodiments provide suppression (or kill rate) of a bacterial population of at least a factor of one hundred in a given amount of time, for instance 1 hr, 2 hr, 4 hr, 10 hr, 12 hr, 15 hr, 20 hr, 24 hr.

Figure 16:
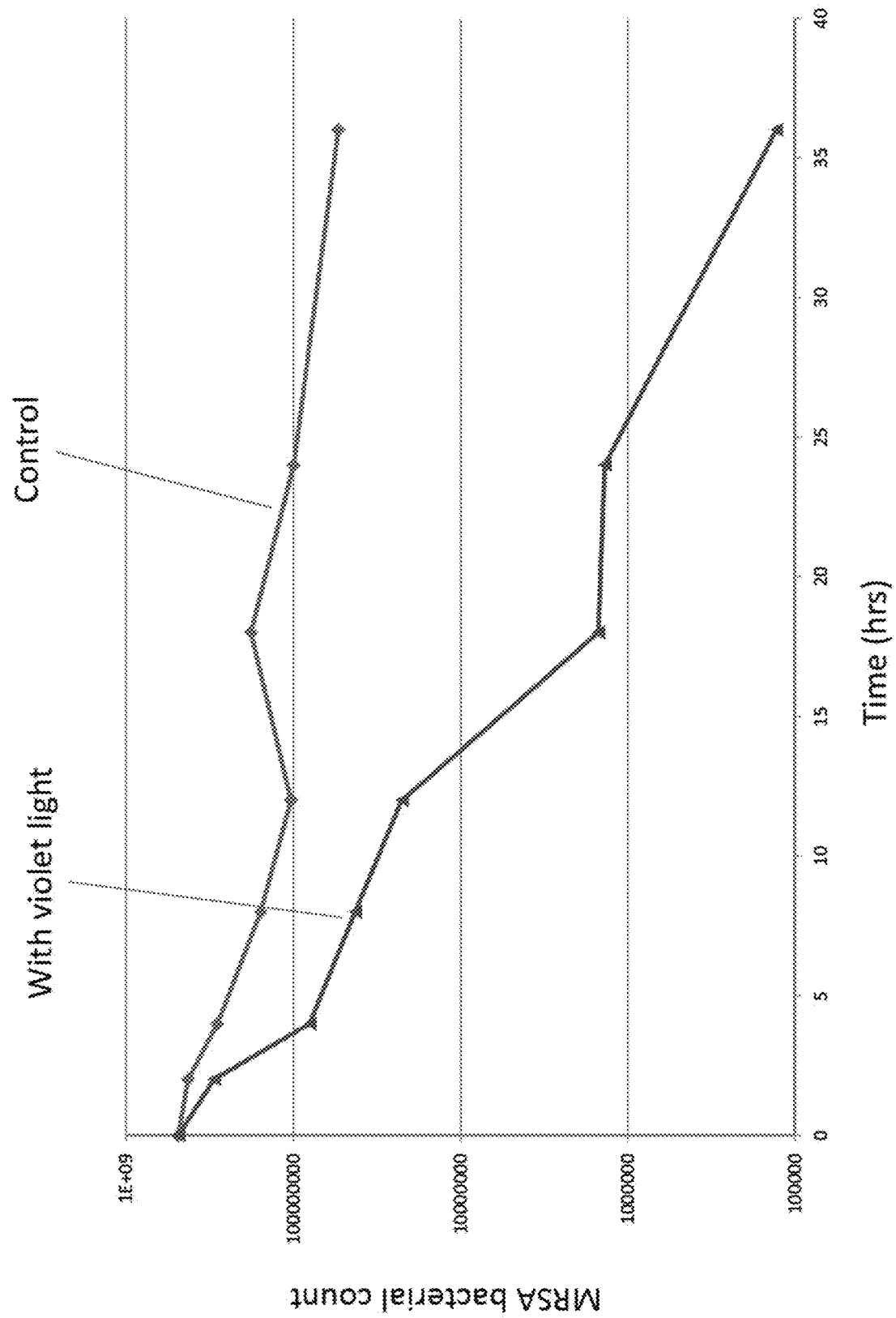
FIG. 16 illustrates experimental results of white light on bacteria according to one or more embodiments of the invention.

FIG. 16 shows experimental results of white light on bacteria. FIG. 16 is similar to FIG. 15, but the light source is white light according to an embodiment of the invention. It has a CCT of about 3800 K. This spectrum is not exactly on-Planckian; however, one skilled in the art would know how to configure similar embodiments targeted to be on-Planckian (or at other desired chromaticities) according to the teachings of this disclosure. The lamp's SPD has 36% violet content in the range 390-420 nm. The lamp has an input power of 9W. It has a spot beam with a 10° half-angle. It illuminates a surface (glass slides with bacteria) at a distance of 2 meters. It has an illuminance of about 1,350 lm/m2 near normal incidence, and a luminous equivalent of radiation of about 230. Therefore, the corresponding violet irradiance is about 2 W/m2.

FIG. 16 again shows significant bacterial suppression. A fit of the bacterial suppression yields a population rate P=10^(hrs/10). Therefore, there is 90% suppression (i.e. suppression by a factor of ten) in about ten hours and 99% suppression (i.e. suppression by a factor of a hundred) in about twenty hours.

The lamp configuration in the experiment of FIG. 16 corresponds to an illuminance and a violet irradiance which can be achieved in practical lighting situations. For instance, a lamp with a higher wattage (e.g. 18 W) could be placed at a distance of 3 m from a surface for disinfection (for instance, it may be a spot lamp on a ceiling track) and provide a similar violet irradiance. This geometry and light level may be suitable in domestic lighting applications (for instance to disinfect a sink, or bathroom or kitchen surface) as well as health care applications (hospitals and others).

The present experimental data pertains to MRSA. However, other bactericidal effects are expected, with kill rates of a similar order of magnitude, for other bacterial strains which include *C. Diff., E. Coli, S. Pyogenes.*

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

What is claimed is:

1. A method of reducing bactericidal counts, the method comprising:
    powering a light source to emit emitted light having a chromaticity, said light source comprising a plurality of light emitters including at least one violet solid-state emitter and at least one phosphor, wherein said chromaticity is within a Duv distance of less than 5E-3 from the Planckian locus, wherein said chromaticity and said Duv are calculated using CIE 1964 10° CMFs; and
    configuring said light source to illuminate a surface with said emitted light to reduce a bacterial count by at least a factor of ten in twelve hours.

2. The method of claim 1, wherein the light source is characterized by a second chromaticity and a second distance to the Planckian Duv2, calculated with the 1931 2° CMFs, and Duv2 is larger than 5E-3.

3. The method of claim 1, wherein the surface receives a violet irradiance in the range 390-420 nm of at least 1 W/m2.

4. The method of claim 1, wherein the source has a CRI Ra above 80.

5. The method of claim 1, wherein the violet solid-state emitter has a peak in the wavelength range 400-410 nm.

* * * * *